United States Patent
Sun et al.

(10) Patent No.: US 12,233,406 B2
(45) Date of Patent: Feb. 25, 2025

(54) AUTOMATED SYSTEM FOR HIGH-THROUGHPUT MICROINJECTION OF ADHERENT CELLS

(71) Applicant: City University of Hong Kong, Hong Kong (CN)

(72) Inventors: Dong Sun, Hong Kong (CN); Fei Pan, Hong Kong (CN); Shuxun Chen, Hong Kong (CN); Yang Jiao, Hong Kong (CN)

(73) Assignee: City University of Hong Kong, Hong Kong (CN)

( * ) Notice: Subject to any disclaimer, the term of this patent is extended or adjusted under 35 U.S.C. 154(b) by 876 days.

(21) Appl. No.: 17/393,721

(22) Filed: Aug. 4, 2021

(65) Prior Publication Data

US 2023/0059331 A1    Feb. 23, 2023

(51) Int. Cl.
*B01L 3/02*    (2006.01)
*C12N 15/89*   (2006.01)
(Continued)

(52) U.S. Cl.
CPC .......... *B01L 3/0227* (2013.01); *B01L 3/0237* (2013.01); *C12N 15/89* (2013.01);
(Continued)

(58) Field of Classification Search
None
See application file for complete search history.

(56) References Cited

U.S. PATENT DOCUMENTS 6,063,629 A    5/2000  Lummel
2003/0021017 A1*  1/2003  Eijsackers .............. G02B 21/32
                                                  359/368
(Continued)

FOREIGN PATENT DOCUMENTS

CN    101857850 A    10/2010
CN    107245431 A    10/2017
(Continued)

OTHER PUBLICATIONS

Pan et al., "Automated High-Productivity Microinjection System for Adherent Cells" IEE Robotics and Automation Letters, vol. 5, No. 2, Apr. 2020 (Year: 2020).*
(Continued)

*Primary Examiner* — Maris R Kessel
*Assistant Examiner* — Henry H Nguyen
(74) *Attorney, Agent, or Firm* — S&F/WEHRW

(57) ABSTRACT

Two or more micropipettes are used to increase a microinjection throughput in an automated system for microinjecting adherent cells on a Petri dish. In the system, a motorized stage carrying the Petri dish sequentially visits the cells according to an optimized injection sequence. The sequence is selected by minimizing a total distance traveled by the motorized stage such that each cell is visited once by one of the micropipettes. Using multiple micropipettes advantageously reduces the minimized total distance over using a single micropipette to thereby increase the throughput. The optimized injection sequence is obtained by solving an equality-generalized traveling salesman problem. Each micropipette is mounted on a motorized micromanipulator. The motorized stage and motorized micromanipulators operate coordinately that each micromanipulator goes down or up during movement of the motorized stage to compensate (Continued)

for unevenness between a focus plane and a moving trajectory of the motorized stage.

9 Claims, 15 Drawing Sheets

(51) Int. Cl.
    *G01N 21/64*     (2006.01)
    *G02B 21/16*     (2006.01)
    *G02B 21/26*     (2006.01)
    *G02B 21/32*     (2006.01)
    *G02B 21/36*     (2006.01)

(52) U.S. Cl.
    CPC ..... *G01N 21/6428* (2013.01); *G01N 21/6458* (2013.01); *G02B 21/16* (2013.01); *G02B 21/26* (2013.01); *G02B 21/32* (2013.01); *G02B 21/36* (2013.01); *G01N 2021/6439* (2013.01)

(56) References Cited

U.S. PATENT DOCUMENTS

| | | | |
|---|---|---|---|
| 2007/0087436 A1 | 4/2007 | Miyawaki et al. | |
| 2008/0002868 A1 | 1/2008 | Ando et al. | |
| 2008/0077329 A1* | 3/2008 | Sun | C12M 23/50 702/19 |
| 2008/0268540 A1 | 10/2008 | Ito et al. | |
| 2011/0027885 A1* | 2/2011 | Sun | C12N 15/89 435/375 |
| 2019/0228268 A1* | 7/2019 | Zhang | G06V 10/82 |

FOREIGN PATENT DOCUMENTS

| | | |
|---|---|---|
| CN | 108070618 B | 3/2021 |
| EP | 0332864 B1 | 1/1993 |
| EP | 0992577 B1 | 7/2000 |
| EP | 1985694 B1 | 2/2011 |
| JP | 2005-318851 A | 11/2005 |

OTHER PUBLICATIONS

Taiwo et al., "Application of Genetic Algorithm to Solve Traveling Salesman Problem", International Journal of Advance Research, vol. 1, Issue 4, Apr. 2013 (Year: 2013).*

K. Viigipuu and P. Kallio, "Microinjection of Living Adherent Cells by Using a Semi-automatic Microinjection System," Altern. Lab. Anim., vol. 32, No. 4, pp. 417-423, Oct. 2004.

H. Matsuoka et al., "High throughput easy microinjection with a single-cell manipulation supporting robot," J. Biotechnol., vol. 116, No. 2, pp. 185-194, Dec. 2004.

S. Sakai, S. Youoku, Y. Suto, M. Ando, and A. Ito, "Automated high-throughput microinjection system for floating cells," In Proc. SPIE 5699, Imaging, Manipulation, and Analysis of Biomolecules and Cells: Fundamentals and Applications III, San Jose, CA, USA, Apr. 2005, vol. 5699, pp. 59-66.

S. Youoku, Y. Suto, M. Ando, and A. Popp, "Automated microinjection system for adherent cells," in Proc. SPIE 6633, Biophotonics 2007: Optics in Life Science, 663301, Munich, Germany, Jul. 2007, vol. 6633.

P. Kallio, T. Ritala, M. Lukkari, and S. Kuikka, "Injection Guidance System for Cellular Microinjections," Int. J. Robot. Res., vol. 26, No. 11-12, pp. 1303-1313, Nov. 2007.

W. Wang, Y. Sun, M. Zhang, R. Anderson, L. Langille, and W. Chan, "A system for high-speed microinjection of adherent cells," Rev. Sci. Instrum., vol. 79, No. 10, p. 104302, Oct. 2008.

G. Becattini, L. S. Mattos, and D. G. Caldwell, "A Fully Automated System for Adherent Cells Microinjection," IEEE J. Biomed. Health Inform., vol. 18, No. 1, pp. 83-93, Feb. 2013.

J. Liu et al., "Robotic Adherent Cell Injection for Characterizing Cell-Cell Communication," IEEE Trans. Biomed. Eng., vol. 62, No. 1, pp. 119-125, Jul. 2014.

Y. T. Chow et al., "A High-Throughput Automated Microinjection System for Human Cells with Small Size," IEEE/ASME Trans. Mechatron., vol. 21, No. 2, pp. 838-850, Sep. 2015.

\* cited by examiner

AUTOMATED SYSTEM FOR HIGH-THROUGHPUT MICROINJECTION OF ADHERENT CELLS

LIST OF ABBREVIATIONS

AP Average precision
BF Boundary Fi
DIC Differential interference contrast
DNA Deoxyribonucleic acid
E-GTSP Equality-generalized traveling salesman problem
FITC Fluorescein isothiocyanate
FOV Field of view
IoU Intersection over Union
OpenCV Open-source computer vision kit
PI Propidium iodide
RNA Ribonucleic acid
TSP Traveling salesman problem

FIELD OF THE INVENTION

The present invention generally relates to an automated microinjection system for injecting a sample to a plurality of adherent cells on a Petri dish. In particular, the present invention relates to such a system equipped with a plurality of micromanipulators for achieving high throughput in microinjection.

BACKGROUND

Microinjection is a powerful and indispensable technique that introduces femtoliters of membrane-impermeable cargos to or extracts subcellular structures from single cells. Among all cellular research, cell transfection is one of the most important topics where microinjection plays a key role. An ideal cell transfection method should be fast, simple, reproducible, non-toxic, cell-targeted, high-throughput, highly efficient, highly viable, and suitable for various cell lines (especially primary cells, stem cells, and suspension cells). The method should deliver all kinds of cargos without molecular size limitations, such as small molecular drugs and cryoprotectants, proteins and peptides, DNA and RNA, synthetic nanomaterials, bacteria mitochondria, chromosomes, microbeads, sperm, nuclei, and microelectromechanical system devices. Cell microinjection generally satisfies these requirements except for the throughput. For instance, microinjection avoids immunogenicity in viral-mediated delivery, chemical toxicity in chemical-mediated delivery, and a high death rate in electroporation. With microinjection techniques, a precise quantity of multiple types of materials can be delivered directly into transfection-challenged cells, such as primary cells and neuronal cells, which are adherent cells that account for the majority among commonly used cell lines.

A significant challenge for developed microinjection systems of both adherent and suspension cells in mammalian animals is the low throughput compared to other transfection methods, such as viral-mediated delivery, chemical-mediated delivery, and other membrane-disruptive delivery approaches. The primary reason for low throughput is the cumbersome operation in experiments and non-parallel processing limitations with a single micropipette only. Among numerous biomedical applications, at least tens of thousands of transfected cells are required to produce meaningful results, for example, genome editing, high-throughput transfection of DNA, and the measurement of gap junctional intercellular communication.

Although it is possible to expand the number of injected cells to the clinically required amount through cell culture, if the expansion starts with too few cells, the function and viability of the final expanded cells are significantly degraded after several generations of culture. It is also important to note that the low throughput problem cannot be solved by simply running the existing injection equipment for a longer period to obtain a sufficiently larger number of injected cells. The cells in the processing platform can only maintain their vitality for a limited time, and the time interval between different processed cell groups cannot be too long to ensure the consistency of the cell properties. Therefore, high-throughput microinjection enabling at least thousands of cells in each operation cycle is urgently needed in the art. After injection, the cells can be expanded into a therapeutic amount through cell subcultures. The increase of microinjection throughput undoubtedly makes this technique more widely accepted by biology and medicine communities.

SUMMARY OF THE INVENTION

An aspect of the present invention is to provide a system for automatically providing microinjection of a sample to a plurality of adherent cells with provision of a high throughput in microinjection. The plurality of adherent cells is disposed on a Petri dish.

The system comprises a motorized stage for two-dimensionally moving the Petri dish, a plurality of motorized micromanipulators for manipulating a plurality of micropipettes used for injecting the sample to the plurality of adherent cells, and one or more computers for controlling the system. An individual micromanipulator is configured to hold and manipulate one micropipette in the plurality of micropipettes. The one or more computers is configured to control the motorized stage to sequentially visit respective cells in the plurality of adherent cells according to an injection sequence. In particular, the injection sequence is an optimized one selected by minimizing a total distance traveled by the motorized stage to sequentially visit the respective cells such that each of the respective cells is visited once by one micropipette selected from the plurality of micropipettes. In a typical situation that the respective cells are randomly distributed on the Petri dish, using the plurality of micropipettes reduces the minimized total distance over using a single micropipette to thereby increase a throughput of microinjection.

Preferably, the system further comprises an optical microscope for viewing the Petri dish disposed on the motorized stage and a camera for capturing a cell image of the plurality of adherent cells as viewed through the optical microscope. It is also preferable that the one or more computers are further configured to: obtain XY locations of micropipette tips of the plurality of micropipettes; control the camera to capture the cell image; determine, from the cell image, XY locations of the respective cells; and determine the optimized injection sequence according to the XY locations of micropipette tips of the plurality of micropipettes and the XY locations of the respective cells.

In certain embodiments, the one or more computers are further configured to, in determining the XY locations of the respective cells, use a deep learning-based algorithm to perform image segmentation on the respective cells.

Preferably and advantageously, the optimized injection sequence is determined by a computer-implemented process. The process comprises constructing an undirected graph $G=(V,E)$ wherein: $V=\{node(l)|l=0, 1, \ldots, nq\}$ is a set of $nq+1$ nodes, n being a number of cells in the plurality of adherent cells, q being a number of micropipettes in the plurality of micropipettes, V being partitioned into n clusters of nodes, the n clusters of nodes being denoted as $V_0, V_1, \ldots, V_n$, the q micropipettes being denoted as $P_1, P_2, \ldots, P_q$; $E=\{e_{ij}|i, j=0, 1, \ldots, nq\}$ is an edge set representing edges joining node(i) and node(j) with a cost $c_{ij}$ in the graph G; $V_0$ is given by $V_0=\{node(0)\}$ where node(0) represents $P_1$; $V_m$, $m \in \{1, 2, \ldots, n\}$, is given by $V_m=\{node((m-1)q+k)|k=1, 2, \ldots, q\}$, where node((m-1)q+1), node((m-1)q+2), \ldots, node(mq) respectively represent $C_m$, $C'_m(2), \ldots, C'_m(q)$ in which $C_m$ is an mth real cell in the plurality of adherent cells, and $C'_m(k)$, $k \in \{2, \ldots, q\}$, is a kth virtual cell of the mth real cell; $P_k$, $k \in \{1, 2, \ldots, q\}$, has a coordinate $(u_{P_k}, v_{P_k})$ determined from the XY locations of the micropipette tips; $C_m$, $m \in \{1, 2, \ldots, m\}$, has a coordinate $(u_m, u_m)$ determined from the XY locations of the respective cells; $C'_m(k)$, $k \in \{2, \ldots, q\}$, has a coordinate $(u'_m(k), v'_m(k))$ given by $(u'_m(k), v'_m(k))=(u_m+u_{P_1}-u_{P_k}, v_m+v_{P_1}-v_{P_k})$; and $c_{ij}$, i, j $\in \{1, 2, \ldots, nq\}$, is given by a Euclidean distance between node(i) and node(j). The process further comprises: numerically solving an equality-generalized traveling salesman problem (E-GTSP) defined by G to identify an ordered sequence of nodes containing one node from each of $V_0, V_1, \ldots, V_n$ such that the ordered sequence of nodes forms a minimum cost cycle; and obtaining the optimized injection sequence from the ordered sequence of nodes.

In certain embodiments, the solving of the E-GTSP comprises: transforming the E-GTSP to an asymmetric TSP; transforming the asymmetric TSP into a symmetric TSP; and solving the symmetric TSP to yield the ordered sequence of nodes.

The optical microscope may be a fluorescence microscope. The optical microscope may also be an inverted microscope. In certain embodiments, the optical microscope is an inverted fluorescence microscope.

The system may further comprise a plurality of manually rotatable stages for mounting the plurality of motorized micromanipulators.

The individual micromanipulator may comprise a stainless-steel micropipette holder for holding a respective micropipette.

Preferably, the system further comprises a gas pressure provider connectable to an individual micropipette for controllably forcing out the sample present in the individual micropipette. The one or more computers are further configured as follows. When a certain cell in the plurality of adherent cells is visited by a certain micropipette manipulated by a corresponding micromanipulator, the one or more computers control the corresponding micromanipulator to cause said certain micropipette to pierce into said certain cell, and control the gas pressure provider to cause said certain micropipette to inject a predetermined amount of the sample into said certain cell.

Preferably and advantageously, the one or more computers are further configured to control the motorized stage and the plurality of motorized micromanipulators in a coordinated way that the individual micromanipulator goes down or up during movement of the motorized stage to compensate for unevenness between a focus plane of the optical microscope and a moving trajectory of the motorized stage. It is also preferable that the one or more computers are further configured to determine a moving plane of a dish holder plate of the motorized stage for characterizing the unevenness between the focus plane of the optical microscope and the moving trajectory of the motorized stage, whereby the motorized stage and the plurality of motorized micromanipulators are controlled to compensate for the unevenness according to the determined moving plane.

Generally, the one or more computers are further configured to, after microinjection of the plurality of adherent cells is completed, control the motorized stage to move such that the optical microscope originally viewing a first segment of the Petri dish switches to viewing a second segment thereof, the first segment containing the plurality of adherent cells, the second segment containing a next plurality of adherent cells for microinjection after completion of microinjection of the plurality of adherent cells.

In certain embodiments, the plurality of motorized micromanipulators consists of two micromanipulators.

Other aspects of the present invention are disclosed as illustrated by the embodiments hereinafter.

Skilled artisans will appreciate that elements in the figures are illustrated for simplicity and clarity and have not necessarily been depicted to scale.

DETAILED DESCRIPTION

As used herein, "a sample" or "an injection sample" is a substance for injection into an adherent cell unless otherwise stated. The sample is usually prepared in liquid form for injection into the cell. The sample may be a liquid, an emulsion, or a mixture of liquid and minute solids.

Disclosed herein is a system for automatically providing microinjection of a sample to a plurality of adherent cells with provision of a high throughput in microinjection. Particularly, the high throughput is achievable by providing multiple micropipettes for microinjection instead of providing only a single micropipette such that the system only needs to move an adherent cell on the Petri dish to the nearest one of the multiple micropipettes for microinjection. A travel time is thus shortened, leading to an increase in the microinjection throughput.

Figure 1:
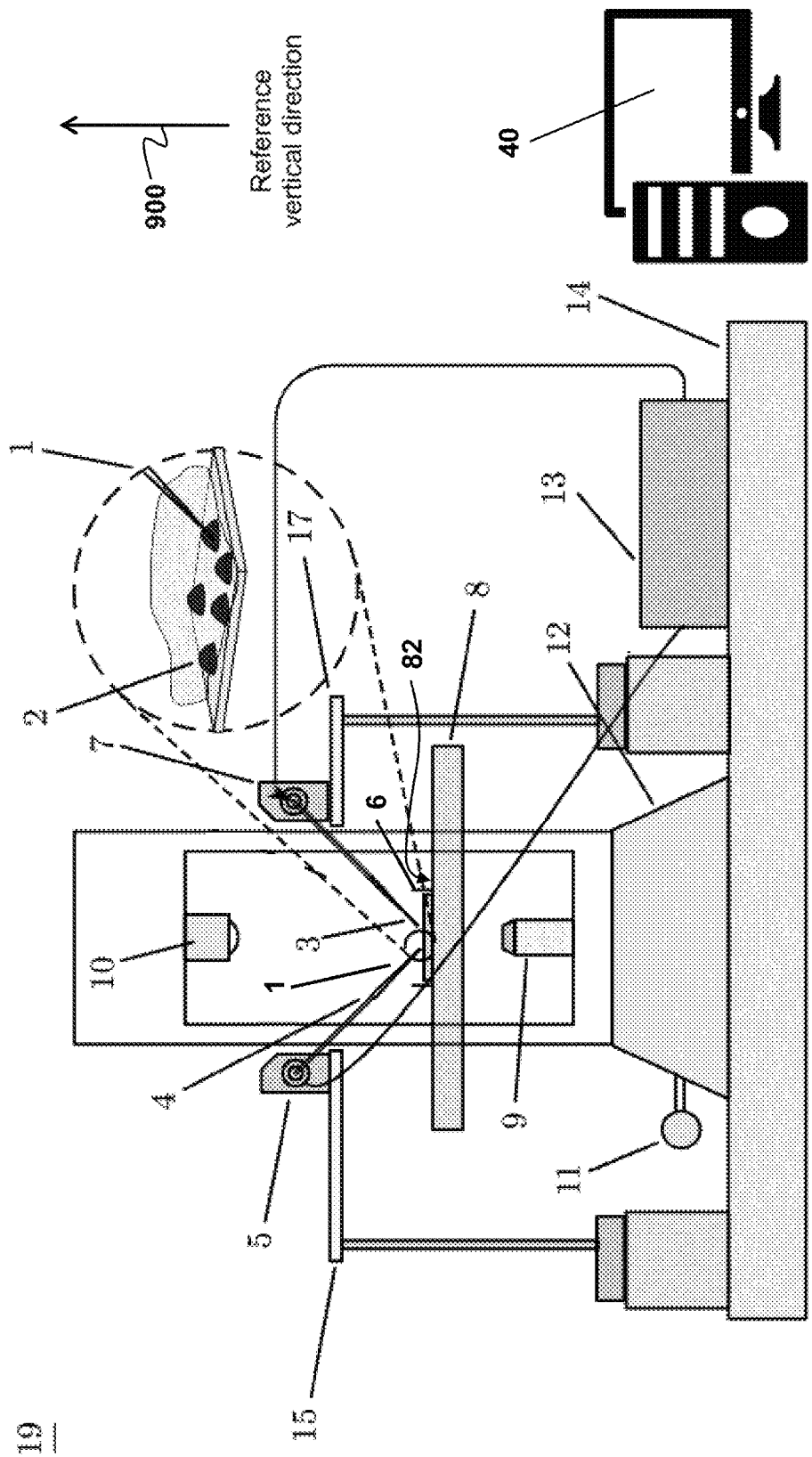
FIG. 1 depicts a schematic diagram of an automated microinjection system for microinjecting adherent cells in accordance with an exemplary embodiment of the present invention.

The disclosed system is exemplarily illustrated with the aid of FIG. 1, which depicts, in accordance with an exemplary embodiment of the present invention, a schematic diagram of an automated microinjection system 19 for automatically injecting a plurality of adherent cells 2 with a sample.

In the automated microinjection system 19 shown in FIG. 1, a specific case of using two micropipettes for microinjection is considered. Using two micropipettes in the system 19 has practical significance over using more than two micropipettes in that using two micropipettes increases a microinjection throughput over using a single micropipette but incurs less manufacturing cost than using more than two micropipettes. Furthermore, the algorithm in determining an optimized injection sequence for the plurality of adherent cells 2 is less computationally complex for the two-micropipette case than the case with more than two micropipettes. Despite the practical significance of the two-micropipette case, the present invention is not limited to the system configuration of using only two micropipettes; the disclosed system may use more than two micropipettes for microinjection during operation.

In operating the system 19 for microinjection, the plurality of adherent cells 2 is disposed on a Petri dish 6. The Petri dish 6 may be a 35 mm glass-bottom Petri dish, where the glass bottom enables the plurality of adherent cells 2 to be observed (by a microscope) from the Petri-dish bottom.

A reference vertical direction 900 is defined as shown in FIG. 1. Herein in the specification and appended claims, positional and directional words such as "above," "below," "higher," "upper," "lower," "top," "bottom" and "horizontal" are interpreted with reference to the reference vertical direction 900.

The automated microinjection system 19 comprises a motorized stage 8, a plurality of motorized micromanipulators 5, 7, and one or more computers 40. The motorized stage 8 is used for two-dimensionally moving the Petri dish 6. The plurality of motorized micromanipulators 5, 7 is used for manipulating a plurality of micropipettes 1, 3. The plurality of micropipettes 1, 3 is used for injecting the sample to the plurality of adherent cells 2. An individual micromanipulator (viz., micromanipulator 5 or 7) is configured to hold and manipulate one micropipette in the plurality of micropipettes 1, 3. The one or more computers 40 are used for controlling the system 19.

Although it is sufficient for the individual micromanipulator (e.g., micromanipulator 5) to move its micropipette (e.g., micropipette 1) up and down for piercing a certain adherent cell while the motorized stage 8 positions this adherent cell right below the micropipette (e.g., micropipette 1), it is preferable and often that the individual micromanipulator (e.g., micromanipulator 5) is capable of moving its micropipette (e.g., micropipette 1) three-dimensionally for offering operational convenience in microinjecting the aforesaid certain adherent cell. In practice, the speed of the individual micromanipulator to three-dimensionally move its micropipette is considerably lower than a running speed of the motorized stage 8 in moving the Petri dish 6. For example, a maximum running speed of 50 mm/s is achievable by the motorized stage 8 whereas the individual micromanipulator may only have a maximum speed of 5 mm/s. Thus, minimizing a total travel time of positioning each cell in the plurality of adherent cell 2 to a corresponding micropipette for achieving the goal of increasing a resultant microinjection throughput is preferably carried out by optimizing an injection sequence for microinjecting the plurality of adherent cells 2 by minimizing a total travel time of the motorized stage 8 in visiting the plurality of adherent cells 2.

In the system 19, the one or more computers 40 are configured to control the motorized stage 8 to sequentially visit respective cells in the plurality of adherent cells 2 according to an injection sequence. Advantageously, the injection sequence is an optimized one selected by minimizing a total distance traveled by the motorized stage 8 to sequentially visit the respective cells such that each of the respective cells is visited once by one micropipette selected from the plurality of micropipettes 1, 3. That is, the optimized injection sequence is obtained by minimizing an objective function that is the total traveled distance of the motorized stage 8 in sequentially visiting all the respective cells in the plurality of adherent cells 2. In practical operations of the system 19, typically the respective cells are randomly distributed on the Petri dish 6. Under this situation of random distribution, using the plurality of micropipettes 1, 3 reduces the minimized total distance over using a single micropipette, thereby increasing a throughput of microinjection achievable by the system 19.

To facilitate automated microinjection, preferably the system 19 is further equipped with a gas pressure provider 13 connectable to an individual micropipette for controllably forcing out the sample present in the individual micropipette. Additionally, the one or more computers 40 are further configured as follows. When a certain cell in the plurality of adherent cells 2 is visited by a certain micropipette manipulated by a corresponding micromanipulator, the one or more computers 40 control the corresponding micromanipulator to cause the aforesaid micropipette to pierce into the aforesaid cell, and control the gas pressure provider 13 to cause the aforesaid micropipette to inject a predetermined amount of the sample into the aforesaid cell.

In determining the optimized injection sequence, a first requisite is to obtain or determine locations of the respective cells in the plurality of adherent cells 2. Determination of these locations is most conveniently accomplished by first acquiring a digital image of the plurality of adherent cells 2, and then using an image processing technique to locate the respective cells. Usually, an optical microscope 12 is installed in the system 19 for viewing the Petri dish 6 that is disposed on the motorized stage 8. Furthermore, a camera 11 is optically coupled to the optical microscope 12 for capturing an image (referred to as a cell image for the sake of convenience) of the plurality of adherent cells 2 as viewed through the optical microscope 12.

With the presence of the camera 11, the one or more computers 40 control the camera 11 to capture the cell image, and determine XY locations of the respective cells from the cell image. The one or more computers 40 also obtain XY locations of micropipette tips of the plurality of micropipettes 1, 3. The XY locations of micropipette tips may be obtained from the cell image, or independently from one or more other images taken by the camera 11. According to the XY locations of micropipette tips of the plurality of micropipettes 1, 3 and the XY locations of the respective cells, the one or more computers 40 determine the optimized injection sequence.

In certain embodiments, the one or more computers 40 are further configured to, in determining the XY locations of the respective cells, use a deep learning-based algorithm to perform image segmentation on the respective cells. "Deep learning" means to use an artificial neural network composed of hundreds, even thousands of layers, to automatically "learn" useful representations from raw data with multiple levels of abstraction. One such artificial neural network for medical image segmentation is a U-net framework. For details of the U-net framework, see O. RONNEBERGER, P. FISCHER and T. BROX, "U-Net: convolutional networks for biomedical image segmentation," in *Medical Image Computing and Computer-Assisted Intervention—MICCAI* 2015, ser. Lecture Notes in Computer Science, N. Navab, J. Hornegger, W. M. Wells, and A. F. Frangi, Eds. Springer International Publishing, 2015, pp. 234-241.

Usually, the optical microscope 12 does not have a FOV sufficiently large enough to cover the entire Petri dish 6. Hence, the plurality of adherent cells 2 is located within the FOV viewable by the optical microscope 12. Other adherent cells outside the FOV are not deemed to be in the plurality of adherent cells 2. In normal practice, the system 19 processes these other adherent cells after the system 19 completes microinjection of the plurality of adherent cells 2. Preferably, the one or more computers 40 are further configured as follows. After microinjection of the plurality of adherent cells 2 is completed, the one or more computers 40 controls the motorized stage 8 to move such that the optical microscope 12 originally viewing a first segment (viz., a first region) of the Petri dish 6 switches to viewing a second segment (viz., a second region) thereof. The first segment contains the plurality of adherent cells 2. The second segment contains a next plurality of adherent cells for microinjection after completion of microinjection of the plurality of adherent cells 2.

The optical microscope 12 may be an ordinary one or may be a special-purpose microscope. In certain embodiments, the optical microscope 12 is a fluorescence microscope for detecting fluorescence emitted by cells as well as observing the cells, especially living cells.

In the art, an inverted microscope is popular for observing living cells under microinjection because a micropipette is located above a Petri dish. Preferably, the optical microscope 12 is an inverted microscope. In certain embodiments, the optical microscope 12 is an inverted fluorescence microscope. Nonetheless, the present invention is not limited to the case that the optical microscope 12 is an inverted microscope; the optical microscope 12 may be an upright microscope.

In certain embodiments, the system 19 further comprises a plurality of manually rotatable stages 15, 17 for mounting the plurality of motorized micromanipulators. Each manually rotatable stage may be three-dimensionally rotatable for providing operational convenience in mounting a respective micromanipulator.

Generally, the individual micromanipulator is installed with a micropipette holder 4 for holding a respective micropipette. The micropipette holder 4 may be, for instance, a stainless-steel micropipette holder.

In certain embodiments, the motorized stage 8 includes a dish holder plate 82 for carrying the Petri dish 6. The dish holder plate 82 is usually a flat plane for the Petri dish 6 to reside on.

The system 19 may be divided into a computer vision subsystem and a robotic control subsystem. The computer vision subsystem comprises the optical microscope 12 and the camera 11. Most experimental operations in using the system 19 may be performed in the diascopic illumination mode under a light source 10 and a 40× objective lens 9. The objective lens 9 is optically coupled to, or is part of, the optical microscope 12. The robotic control subsystem comprises the motorized stage 8 and the plurality of motorized micromanipulators 5, 7 fixed on the plurality of manually rotatable stages 15, 17. In normal operations, the micropipette holder 4 holding the micropipette 1 is attached to the X-axis of the micromanipulator 5. Similarly, the micromanipulator 7 has the same arrangement. Injection pressure is provided by the gas pressure provider 13 for forcing out the sample from the micropipette 1 during microinjection of the plurality of adherent cells 2. The plurality of adherent cells 2 is cultured and injected on the Petri dish 6, which is placed onto the motorized stage 8 throughout the experiment. All the electromechanical components used by the system 19 are placed on an anti-vibration table 14. The one or more computers 40 are used to control different elements of the system 19 for facilitating microinjection of the adherent cells 2. The micropipettes 1, 3, usually made of glass, are replaceable. The micropipette 1 is detachably attachable to the micropipette holder 4. Similarly, the micropipette 3 is detachably attachable to a corresponding micropipette holder installed in the motorized manipulator 7.

Figure 2:
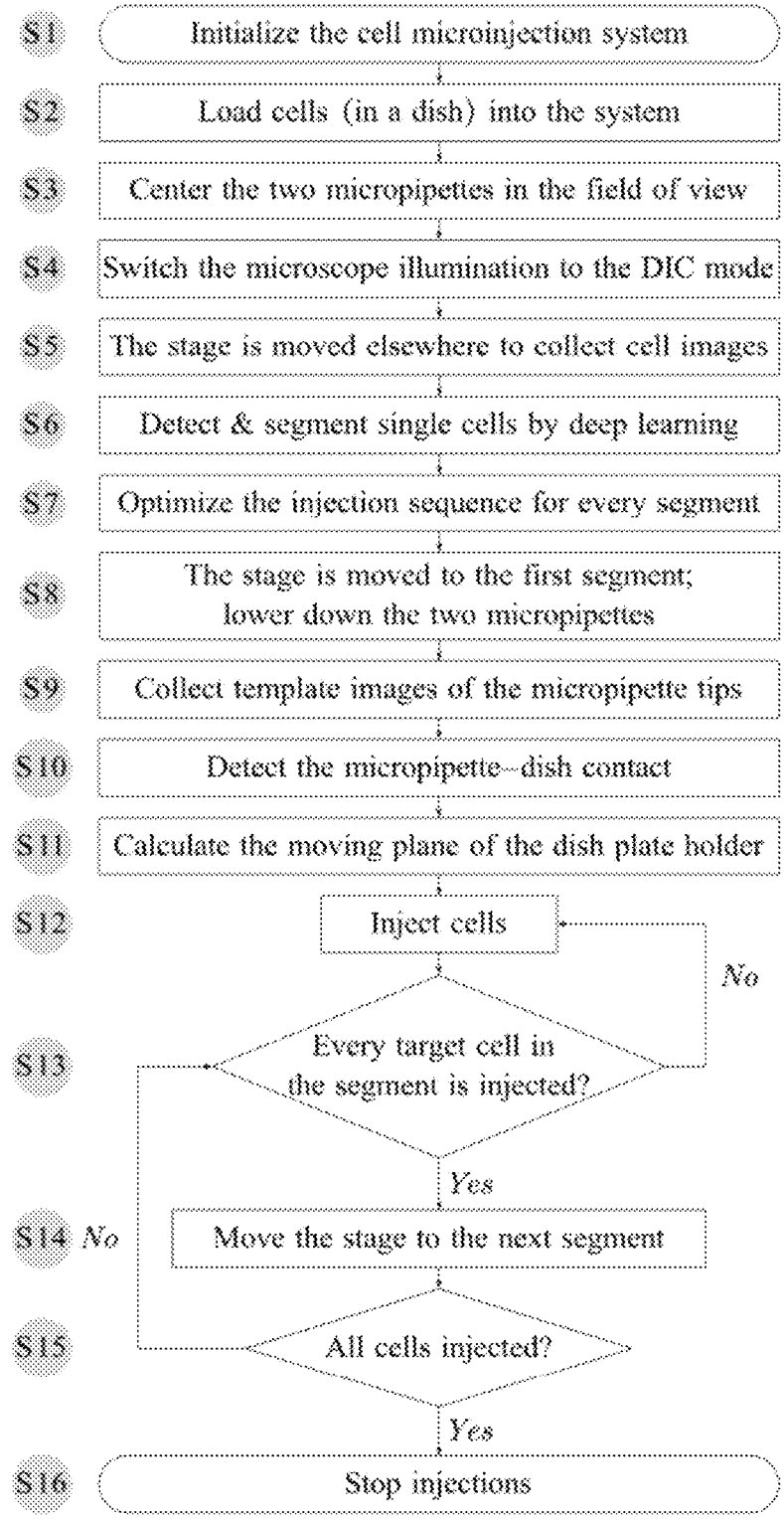
FIG. 2 depicts a flowchart showing a working procedure of microinjecting the adherent cells with the system of FIG. 1.

FIG. 2 depicts a flowchart showing a procedure of automated microinjection for the automated microinjection system 19. First, the system 19 is initialized (S1). Second, adherent cells cultured in the Petri dish 6 having a glass bottom are transferred from an incubator onto the motorized stage 8 and positioned over the optical microscope 12 (S2). Third, the micropipettes 1, 3 filled with injection samples are installed onto the two micromanipulators 5, 7 and lowered to a focus plane in a FOV of the optical microscope 12 (S3). Fourth, if the optical microscope 12 is equipped with the DIC mode, switch to the DIC mode for enhancing the contrast of adherent cells to help distinguishing different cells (S4). Fifth, the motorized stage 8 moves from segment to segment of the Petri dish 6 to collect images (S5). Each segment is a physical rectangular region of the dish bottom corresponding to a FOV of the optical microscope 12 as reflected in an individual image taken by the camera 11. Sixth, cell images are analyzed for detection and segmentation (S6). Seventh, injection sequences in each segment are optimized (S7). Eighth, the motorized stage 8 is moved back to the first segment; the micropipettes 1, 3 are lowered down to the dish bottom (S8). Ninth, each micropipette tip's template image is collected for automatically detecting tip-dish contact in the tenth step S10 in the working flow (S9). Tenth, automatic micropipette-dish contact is performed to collect information of the penetration depth (S10). Eleventh, the moving plane of the dish holder plate 82 relative to each micromanipulator is calculated (S11). After completing the preparations, cell microinjection can start (S12). If every target cell in a segment has been injected (S13), then the motorized stage 8 moves to the next segment (S14) to continue microinjection. If all the detected cells are injected (S15), the system stops (S16).

Figure 3:
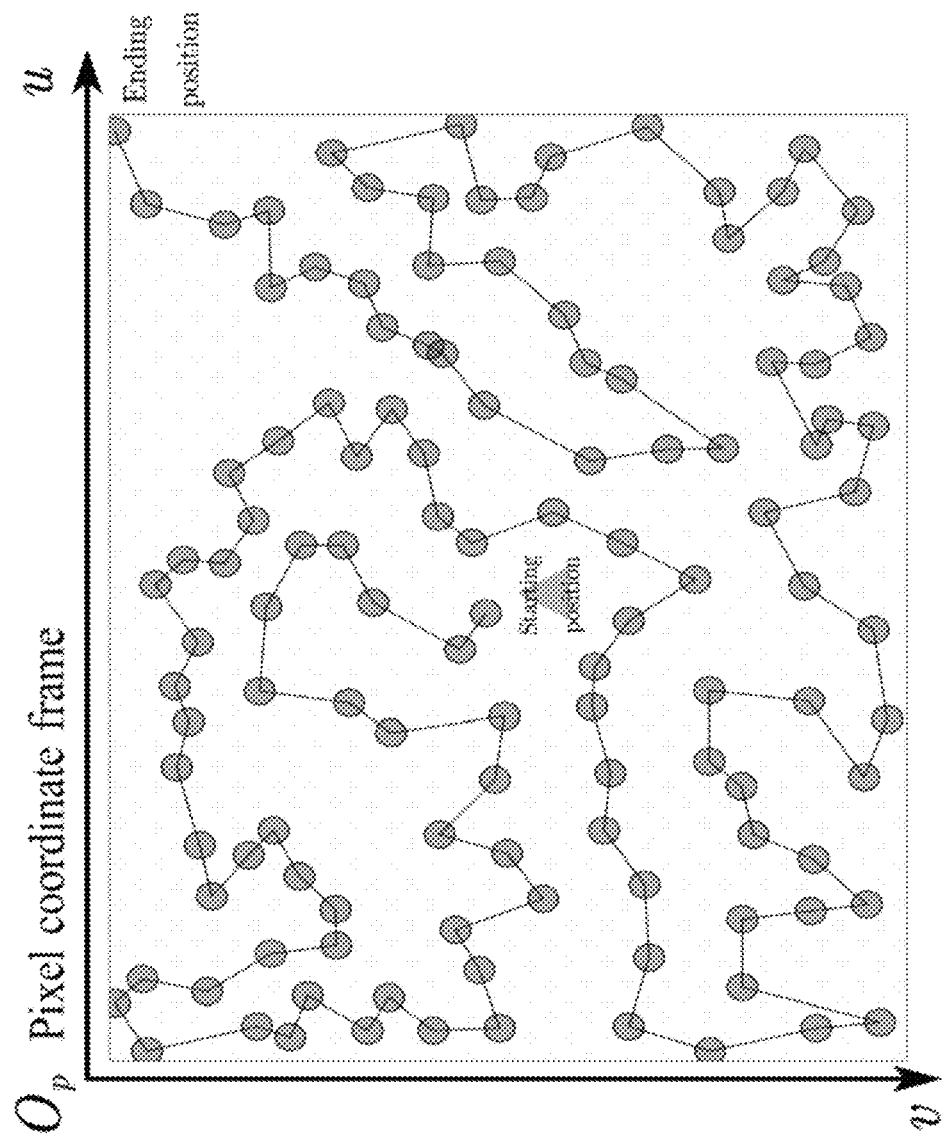
FIG. 3 shows an example of an optimized injection path of one micropipette injecting over one hundred cells under 20× magnification.

FIG. 3 shows an example of an optimized injection path of one micropipette injecting over one hundred cells under 20× magnification, where the optimized injection path is shown on a microscope-taken image with respect to a pixel coordinate frame as a frame of reference. Optimization of the injection path can improve productivity, where the optimization is done by minimizing the path length. The injection should start from the cell nearest to the micropipette tip until the farthest one in the shortest path. This process is an asymmetric TSP (n+1 nodes), which can be transformed to a symmetric TSP (2n+2 nodes) for solving the asymmetric TSP. The position of the tip in the pixel coordinate frame is denoted by $(u_0, v_0)$. The positions of n cells are denoted by $(u_i, v_i)_{i=1,\ldots,n}$. Let $D_{(n+1)\times(n+1)}$ be the distance matrix of the sequence of nodes (cells) $(u_i, v_i)_{i=0,\ldots,n}$, where $d_{ij}=\sqrt{(u_i-u_j)^2+(v_i-v_j)^2}$. The matrix $D_{(n+1)\times(n+1)}$ is symmetric and non-negative. To ensure the optimized path to start from $(A_0, B_0)$, one sets all the distances to node 0 to zero, such that $D_{(n+1)\times(n+1)}$ becomes $\tilde{D}_{(n+1)\times(n+1)}$. Let $\tilde{d}_{max}$ be $\tilde{d}_{max}=\max(\tilde{d}_{ij})$, and transform $\tilde{D}_{(n+1)\times(n+1)}$ to $D'_{(n+1)\times(n+1)}$ as follows:

$$d'_{ij} = \begin{cases} 0 & \text{if } i = j \\ \tilde{d}_{ij} + 3\tilde{d}_{max} + \varepsilon & \text{otherwise,} \end{cases} \quad (1)$$

where $\varepsilon>0$ is a small positive number. The asymmetric distance matrix $D'_{(n+1)\times(n+1)}$ is then used to construct a symmetric distance matrix $\bar{D}_{(2n+2)\times(2n+2)}$ as $$\bar{D} = \begin{bmatrix} \infty & (D')^T \\ D' & \infty \end{bmatrix}_{(2n+2)\times(2n+2)} \quad (2)$$

where $\infty$ is replaced by a large positive matrix. The matrix $\bar{D}$ acquires the optimized injection path. The mapping between nth and (n−1)th cells is $(u_n-u_{n-1}+u_0, v_n-v_{n-1}+v_0)$. In one experimental finding, the optimization was completed in about 0.1 s only.

Figure 4:
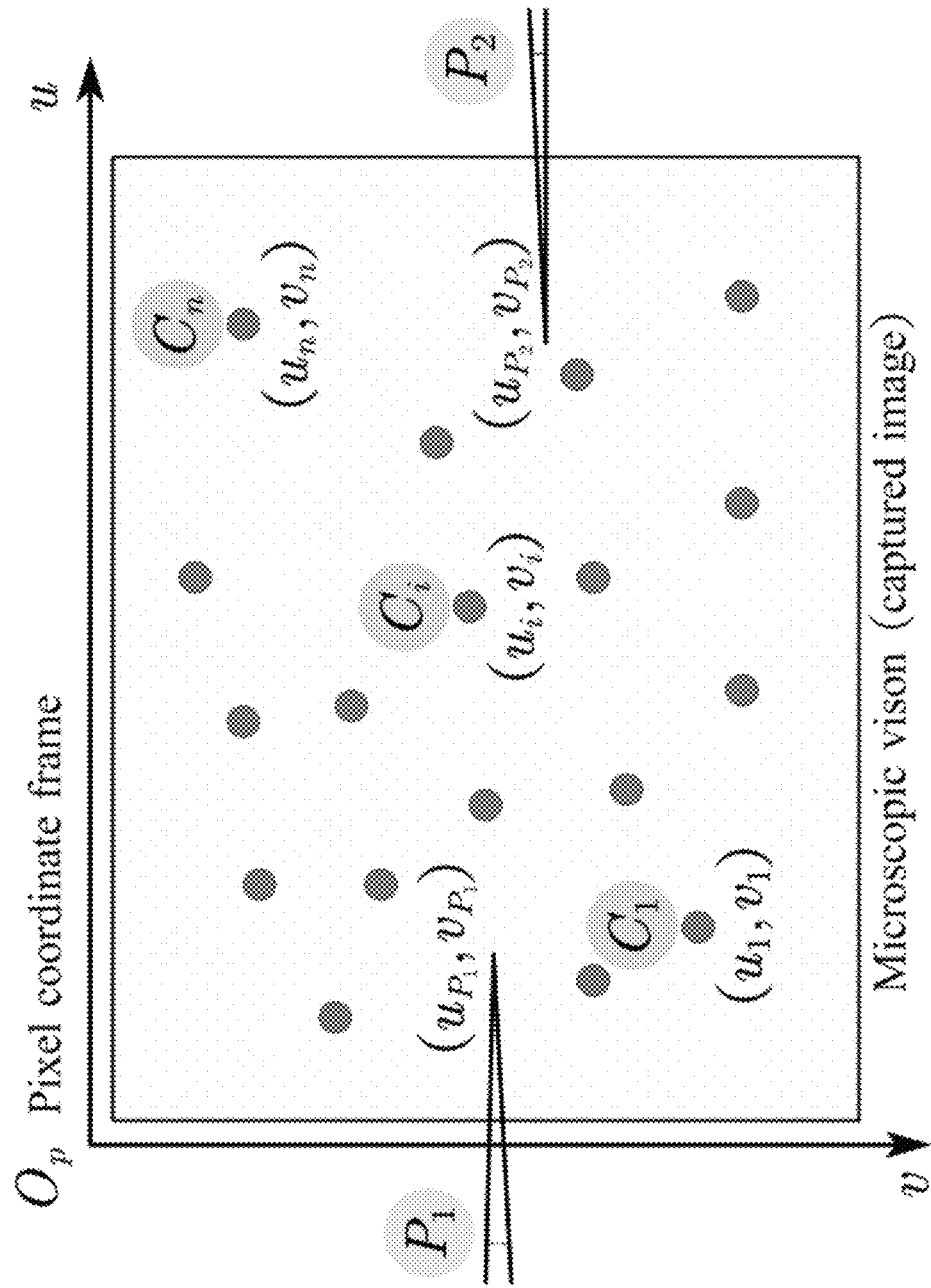
FIG. 4 shows a random distribution of adherent cells, and two oppositely disposed micropipettes for microinjecting the cells.

FIG. 4 is an image showing a random cell distribution and two opposite micropipettes. Guiding both micropipettes to inject only nearby cells to save time is reasonable in an ideal situation. In operating the automated microinjection system 19, however, it is more practical that the system 19 inserts the sample to one cell at a time instant by one micropipette to avoid optimization of the injection sequence to become an overly complex task that burdens the one or more computers 40. That is, a cell is injected either by the left micropipette $P_1$ or by the right micropipette $P_2$ but not both. As a result, the optimized injection sequence is aligned with the minimized total distance traveled by the motorized stage 8. As will be shown later, the optimized injection sequence can be obtained by solving an E-GTSP.

Figure 5:
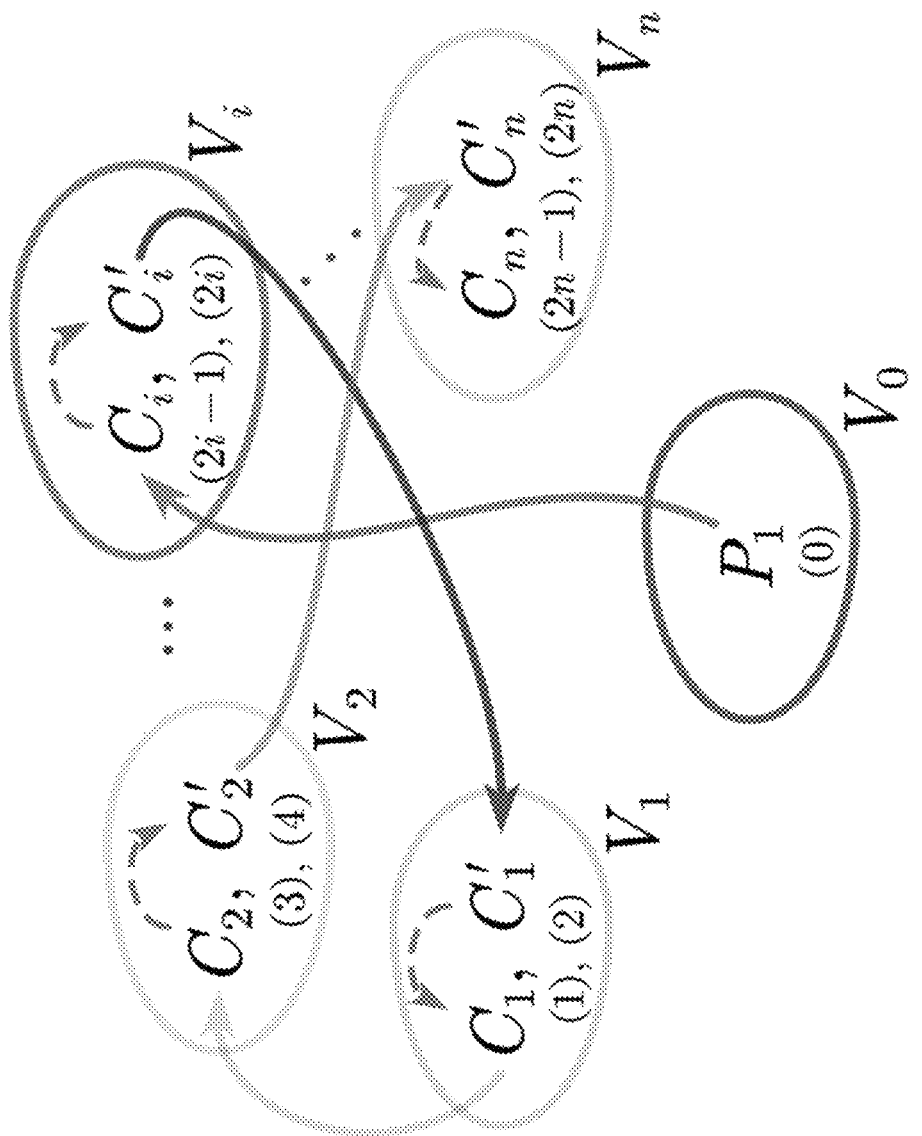
FIG. 5 is a state diagram showing the formulation of optimization problem for two micropipettes visiting adherent cells, where the optimization problem is formulated as an E-GTSP.

FIG. 5 shows the formulation of the optimization problem for the two micropipettes ($P_1$ and $P_2$) and cells into an E-GTSP. Given a weighted complete directed or undirected graph G=(V, E) and a partition $V_0, V_1, \ldots, V_n$ (cluster) of the overall node-set V, a minimum cost cycle containing precisely one node from each cluster $V_0, V_1, \ldots, V_n$ is identified. The overall node-set V={node(i)|i=0, 1, . . . , n}∪{all corresponding virtual nodes} contains every node and the edge set E={$e_{ij}$} represents edges joining node(i) to node(j) with a cost $c_{ij}$ in the graph G. Denote detected cells as $C_1, C_2, \ldots, C_n$.

Theorem 1. The distance traveled by the motorized stage 8 for injection of a cell $C_m$ by the micropipette $P_2$ is equivalent to the distance for injection of a virtual cell $C'_m$ with a new coordinate $(u'_m, v'_m)=(u_m+u_{P_1}-u_{P_2}, v_m+v_{P_1}-v_{P_2})$ by the micropipette $P_1$.

Proof Since it is desired to arrange the overall injection sequence to minimize the distance traveled by the motorized stage 8, it is required to know which cell(s) should be injected by which micropipette and when to switch to the other after injecting a cell by a preceding micropipette. The key to answering the two questions lies in analyzing the distance of the motorized stage 8 when switching of the micropipettes is performed for injecting cells that are far apart. Without loss of generality, suppose that the micropipette first injects a nearby cell called $C_l$, then the micropipette $P_2$ injects one of its nearby cells $C_m$, and then the micropipette $P_1$ injects its second nearby cell $C_q$. In such case, the motorized stage 8 first moves the cell $C_l$ to the reference position of the micropipette $P_1$ for penetration, then moves the cell $C_m$ to the reference position of the micropipette $P_2$, and then moves the cell $C_q$ back to the reference position of the micropipette $P_1$. The distance traveled by the motorized stage 8, denoted as $d_{total}$, is given by $$d_{total}=d_{C_l \to Ref.\ pos.\ P_1}+d_{C_m \to Ref.\ pos.\ P_2}+d_{C_q \to Ref.\ pos.\ P_1} \quad (3)$$

where $$d_{C_l \to Ref.\ pos.\ P_1}=\sqrt{(u_l-u_{P_1})^2+(v_l-v_{P_1})^2}, \quad (4)$$

$$d_{C_m \to Ref.\ pos.\ P_2}=[(u_l+(u_m+u_{P_1}-u_{P_2}))^2+(v_l+(v_m+v_{P_1}-v_{P_2}))^2]^{1/2} \quad (5)$$

and $$d_{C_q \to Ref.\ pos.\ P_1}=[((u_m+u_{P_1}-u_{P_2})-u_q)^2+(v_m-v_{P_1}-v_{P_2})-v_q)^2]^{1/2}. \quad (6)$$

It can be inferred from (5) and (6) that the injection of a cell $C_m$ by the micropipette $P_2$ is equivalent to the injection of a virtual cell $C'_m$ with a new coordinate $(u'_m, v'_m)=(u_m+u_{P_1}-u_{P_2}, v_m+v_{P_1}-v_{P_2})$ by the micropipette $P_1$, in terms of the distance traveled by the motorized stage 8. As such, in a series of n cells, determining which cells to be injected by the micropipette $P_2$ can be reformulated to forcing the micropipette $P_1$ to choose either a real cell, for example, $C_m$ or its virtual opponent $C'_m$. ∎

As a consequence, denote the reference position of the micropipette $P_1$ as node(0), the position of the cell $C_i$ as node(2i−1), and the position of the corresponding virtual cell $C'_i$ as node(2i) for i=1, 2, . . . , n. The node(0) is in the cluster $V_0$ and the two nodes (2i−1) and (2i) are in the cluster $V_i$, as shown in FIG. 5. The cost $c_{ij}$ of an edge $e_{ij}$ between node(i) and node(j) is calculated as the Euclidean distance $d_{ij}=\sqrt{(u_i-u_j)^2+(v_i-v_j)^2}$, i,j=0, 1, . . . , n, which forms the undirected graph G=(V, E) with V={node (i)|i=0, 1, . . . , n} and E={edge $e_{ij}$ with a cost $c_{ij}=d_{ij}$}. In the E-GTSP, any qualified cycle in the graph G visits precisely one node from each cluster, which means either a real cell $C_i$ or its virtual opponent $C'_i$ should be chosen, which further judges whether cell $C_i$ will be injected by micropipette $P_1$ or by $P_2$.

Finding an optimized solution requires transforming the E-GTSP to a standard TSP. First, all costs inside each cluster are set to zero, i.e. $c_{(2i-1)(2i)}=d_{(2i-1)(2i)}=d_{(2i)(2i-1)}=0$, to ensure that the optimized cycle enters a cluster $V_i$ at node (2i−1) (or node(2i)) and then exits from the other node, node(2i) (or node(2i−1)). Second, the costs from node(2i−1) to the other nodes outside the cluster $V_i$ and the costs from node(2i) to the other nodes outside the cluster $V_i$ are exchanged. More precisely, $$c_{(2i-1)q}=d_{(2i)q}=\sqrt{(u_{2i}-u_q)^2+(v_{2i}-v_q)^2}, q\notin V_i, i=1,2,\ldots,n, \quad (7)$$

and $$c_{(2i)q}=d_{(2i-1)q}=\sqrt{(u_{2i-1}-u_q)^2+(v_{2i-1}-v_q)^2}, q\notin V_i, i=1,2,\ldots,n. \quad (8)$$

Third, all costs from other nodes to node(0) are set to zero to ensure that the optimized tour starts from the reference position of the micropipette $P_1$ but not the return. After the above three steps are done, the E-GTSP is transformed into an asymmetric TSP with a distance matrix denoted by $\tilde{D}_{(2n+1)\times(2n+1)}$. Let $\tilde{d}_{max}$ be given by $\tilde{d}_{max}=\max(\tilde{d}_{ij})$, and then transform the matrix $\tilde{D}_{(2n+1)\times(2n+1)}$ to the matrix $D'_{(2n+1)\times(2n+1)}$ as follows:

$$d'_{ij} = \begin{cases} 0 & \text{if } i = j \\ \tilde{d}_{ij} + 3\tilde{d}_{max} + \varepsilon & \text{otherwise,} \end{cases} \quad (9)$$

where $\varepsilon \leq 0$ is a small positive number.

The asymmetric distance matrix $D'_{(2n+1)\times(2n+1)}$ is used to construct a symmetric distance matrix $\bar{D}_{(4n+2)\times(4n+2)}$ as $$\bar{D} = \begin{bmatrix} \infty & (D')^T \\ D' & \infty \end{bmatrix}_{(4n+2)\times(4n+2)} \quad (10)$$

where $\infty$ is replaced by a large positive matrix. The one or more computers 40 solve the matrix $\bar{D}$ and obtains the optimized injection sequence starting from the micropipette $P_1$ or the micropipette $P_2$.

Figure 6:
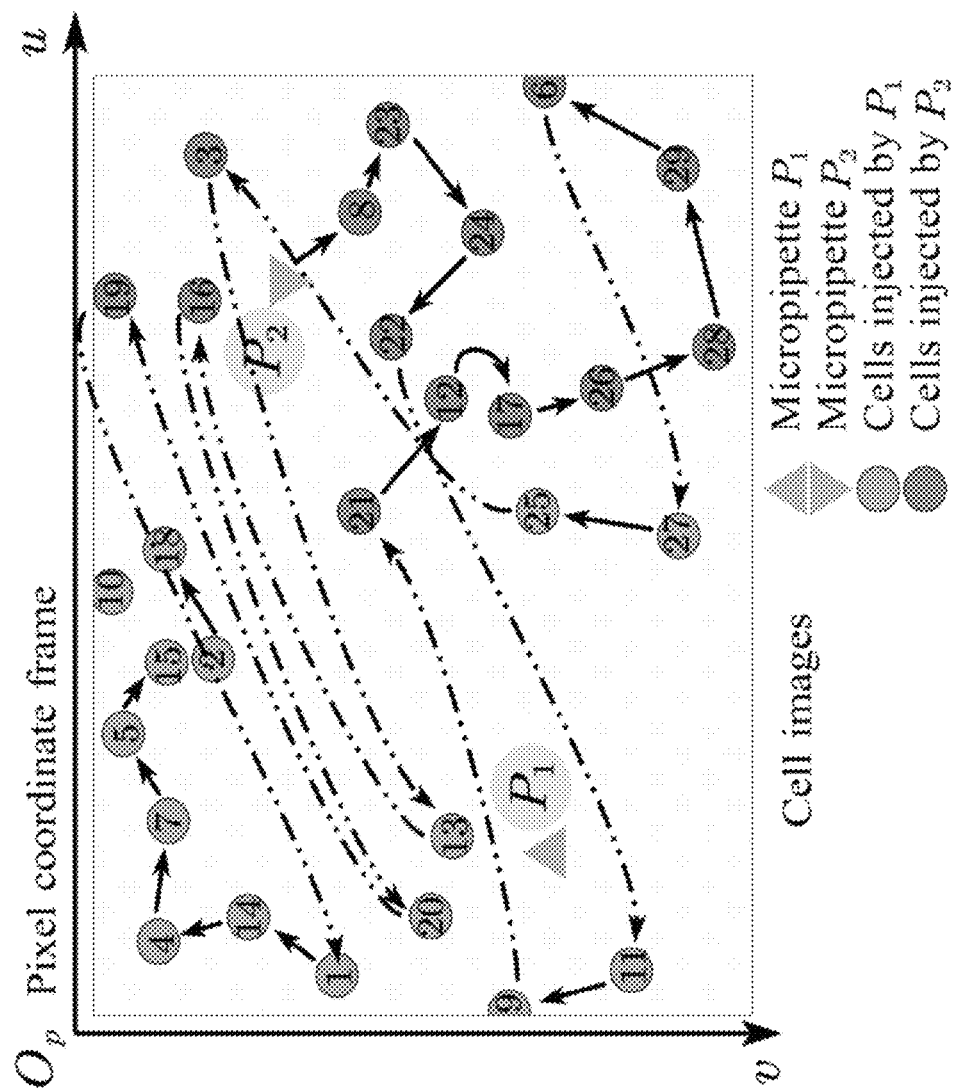
FIG. 6 shows an example of an optimized injection path of two micropipettes injecting 29 cells under 40× magnification.

FIG. 6 shows an example of an optimized injection path of two micropipettes injecting 29 cells under 40× magnification, where the optimized injection path is shown on an image with respect to a pixel coordinate frame used as a frame of reference. Solid arrows represent consecutive injections by one micropipette while dashed arrows represent a switch to the other micropipette. The injection starts from the cell $C_8$ and then $C_{23}$, $C_{24}$ and $C_{22}$ consecutively by using the micropipette $P_2$. After injecting these nearby cells of $P_2$, the system starts to inject cells $C_{11}$ and $C_9$ by using the micropipette $P_1$. Then, the system injects cells $C_{21}$, $C_{12}$, $C_{17}$, $C_{26}$, $C_{28}$, $C_{29}$ and $C_6$ by the micropipette $P_2$. Soon, cells $C_{27}$ and $C_{25}$ will be injected by the micropipette $P_1$ while the cell $C_3$ will be injected by the micropipette $P_2$. After that, the micropipette $P_1$ injects the cell $C_{13}$ while the micropipette $P_2$ injects the cell $C_{16}$. Again, the micropipette $P_1$ injects the cell $C_{20}$ while the micropipette $P_2$ injects the cell $C_{19}$. Finally, all the remaining cells $C_1$, $C_{14}$, $C_4$, $C_7$, $C_5$, $C_{15}$, $C_2$, $C_{18}$ and $C_{10}$ are injected by the micropipette $P_1$. In this case, the total distance traveled by the motorized stage is 777 μm. However, if the micropipette $P_1$ injects all the cells, the optimized injection sequence is $C_{19}$, $C_{16}$, $C_3$, $C_8$, $C_{23}$, $C_{24}$, $C_6$, $C_{29}$, $C_{28}$, $C_{26}$, $C_{27}$, $C_{25}$, $C_{17}$, $C_{12}$, $C_{22}$, $C_{21}$, $C_{18}$, $C_{10}$, $C_2$, $C_{15}$, $C_5$, $C_7$, $C_4$, $C_{14}$, $C_1$, $C_{20}$, $C_{13}$, $C_9$ and $C_{11}$, of which the minimum distance is 980.25 μm. If the micropipette $P_2$ injects all the cells, the optimized injection sequence is $C_{11}$, $C_9$, $C_{13}$, $C_{20}$, $C_1$, $C_{14}$, $C_4$, $C_7$, $C_5$, $C_{15}$, $C_2$, $C_{10}$, $C_{18}$, $C_{21}$, $C_{22}$, $C_{12}$, $C_{17}$, $C_{25}$, $C_{27}$, $C_{26}$, $C_{28}$, $C_{29}$, $C_6$, $C_{24}$, $C_{23}$, $C_8$, $C_3$, $C_{19}$ and $C_{16}$, of which the minimum distance is 1037.25 μm. Obviously, the collaborative operation of the two micropipettes results in a smaller distance than any single micropipette does. The optimization is critical to the overall injection performance.

Based on the foregoing discussion on setting up the E-GTSP for the two-micropipette case, extension to a general situation that the system 19 employs q micropipettes, $q \geq 2$, in the plurality of micropipettes for microinjection is detailed as follows.

The q micropipettes are denoted as $P_1$, $P_2$, ..., $P_q$. The micropipette $P_k$, $k \in \{1, 2, \ldots, q\}$ has a coordinate $(u_{P_k}, v_{P_k})$ on the pixel coordinate frame. The coordinates for the q micropipettes are determined from the XY locations of the micropipette tips. Denote n as a number of cells in the plurality of adherent cells 2. It follows the n adherent cells are denoted as $C_m$, m=1, 2, ..., n. The cell $C_m$ has a coordinate $(u_m, v_m)$ determined from the XY locations of the respective cells.

The E-GTSP for the case of using q micropipettes is formulated by constructing an undirected graph G=(V, E) where V is the overall node-set and E is the edge set.

The overall node-set V is a set of nq+1 nodes and is denoted by V={node(l)|l=0, 1, ..., nq}. In addition, V is partitioned into n non-overlapping clusters of nodes. The n clusters of nodes are denoted as $V_0$, $V_1$, ..., $V_n$. The cluster $V_0$ has one node and is given by $V_0$={node(0)} where node(0) represents $P_1$, the reference micropipette. The cluster $V_m$, $m \in \{1, 2, \ldots, n\}$, has q nodes and is given by $V_m$={node((m−1)q+k)|k=1, 2, ..., q}, where node((m−1)q+1), node((m−1)q+2), ..., node(mq) respectively represent $C_m$, $C'_m(2)$, $C'_m(3)$, ..., $C'_m(q)$. In the last expression, $C_m$ is the mth (real) cell in the plurality of adherent cells 2, and $C'_m(k)$ is the kth virtual cell of the mth real cell. The injection of a cell $C_m$ by the micropipette $P_k$ is equivalent to the injection of a virtual cell $C'_m(k)$ with new coordinates $(u'_m(k), v'_m(k))=(u_m+u_{P_1}-u_{P_k}, v_m+v_{P_1}-v_{P_k})$ by the micropipette $P_1$, in terms of the distance traveled by the motorized stage 8. Note that each of the aforementioned new coordinates is obtained by an application of Theorem 1.

The edge set E={$e_{ij}$|i, j=0, 1, ..., nq} represents edges joining node(i) and node(j) with a cost $c_{ij}$ in the graph G. Values of $c_{ij}$ and $c_{ji}$ are same and are equal to the Euclidean distance $d_{ij}$ between entities at node(i) and at node(j), where $d_{ij}=(u_i-u_j)^2+(v_i-v_j)^2$ for i, j ∈ {1, 2, ..., nq}.

With G constructed, one can make use of an algorithm known in the art for numerically solving the E-GTSP defined by G to identify an ordered sequence of nodes containing one node from each of $V_0$, $V_1$, ..., $V_n$ such that the ordered sequence of nodes forms a minimum cost cycle. Finally, the optimized injection sequence can be obtained from the ordered sequence of nodes.

Algorithms for solving E-GTSP can be found from, for example: K. HELSGAUN, "Solving the equality generalized traveling salesman problem using the LinKernighan-Helsgaun Algorithm," *Mathematical Programming Computation* (2015) 7:269-287; and C.-M. PINTEA, P. C. POP and C. CHIRA, "The generalized traveling salesman problem solved with ant algorithms," *Complex Adaptive System Modeling* (2017) 5:8. The two aforementioned disclosures are incorporated herein by reference. Alternatively, the E-GTSP can be solved by: transforming the E-GTSP to an asymmetric TSP; transforming the asymmetric TSP into a symmetric TSP; and numerically solving the symmetric TSP to yield the ordered sequence of nodes. This approach is detailed above for the specific case of q=2. Algorithms for transforming the E-GTSP to the symmetric TSP for a general value of q can be found in the art, e.g., from C. E. NOON and J. C. BEAN, "An Efficient Transformation of the Generalized Traveling Salesman Problem," *Information Systems and Operational Research*, vol. 31, no. 1, February 1993, pp. 39-44, the disclosure of which is incorporated herein by reference.

Figure 7:
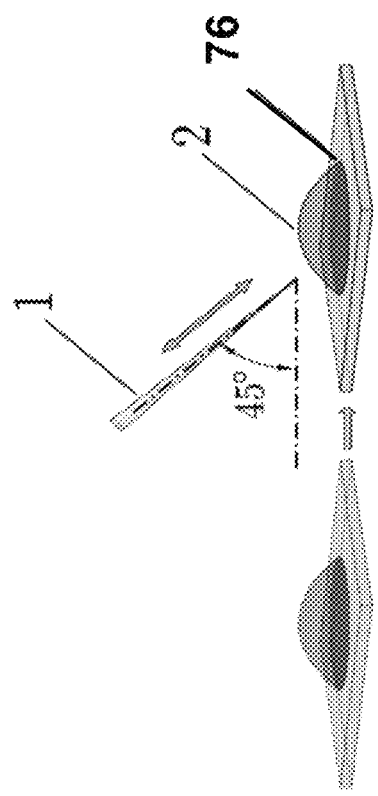
FIG. 7 shows the movement and coordination of a micropipette and a motorized stage when injecting cells.

FIG. 7 shows the movement and coordination of the micropipette 1 and the motorized stage 8 when injecting cells. The X-axis of the micromanipulator 5 is tilted to 45° relative to the horizontal level, causing the micropipette 1 to be tilted by 45°. Before microinjection starts, a reference position of the micropipette tip $(A_0, B_0)$, $(x_r, y_r, z_r)$, $(X_r, Y_r)$ is recorded when the tip touches the dish bottom 76. Here, $(A_0, B_0)$ denotes the tip position in the pixel coordinate frame, $(x_r, y_r, z_r)$ is the reference position of the tip, and $(X_r, Y_r)$ is the reference position of the motorized stage 8. During microinjection, the X-axis of the micromanipulator 5 is withdrawn back by 20 μm $(x_r-20, y_r, z_r)$ first, and the target cell 2 is moved to the reference position $(X_r, Y_r)$. Finally, the X-axis of the micromanipulator 5 pushes the micropipette 1 forward to the reference position $(x_r, y_r, z_r)$ to pierce the cell 2.

Figure 8:
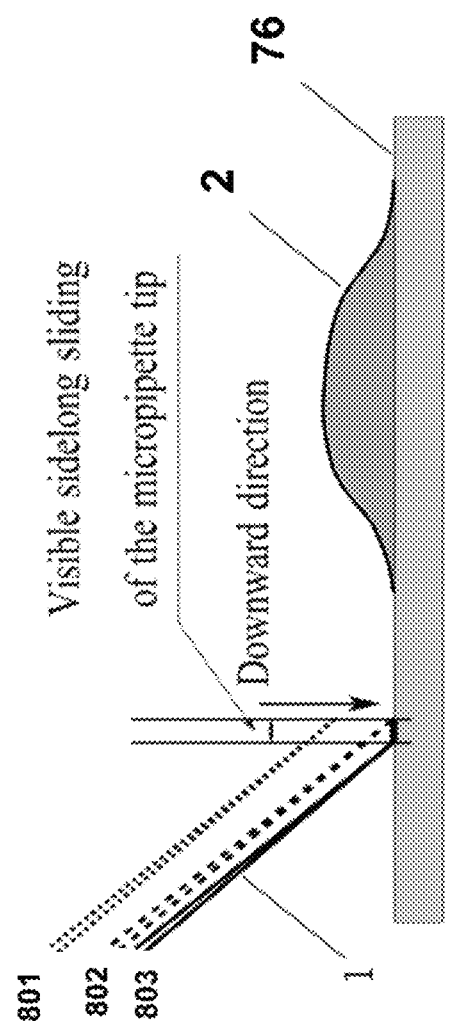
FIG. 8 shows an undesirable generation of sidelong sliding when a micropipette tip touches a dish bottom and continues to go down.

FIG. 8 shows the generation of sidelong sliding when the micropipette tip touches the dish bottom 76 and continues to go down. A common approach to know the tip depth is to manually lower down the micropipette 1 until its tip touches the dish bottom 76 and is deformed to generate noticeable sidelong displacement. It is time-consuming and prone to errors even for an experienced operator, often causing micropipettes to break.

In the automated microinjection system 19, this tip-depth determination operation is automated to improve accuracy and save time by matching a template image to source images recursively in four steps. Positions 801 to 803 as indicated in FIG. 8 show the generation of the sidelong sliding when the tip touches the dish bottom 76 and continues to go down.

Figure 9:
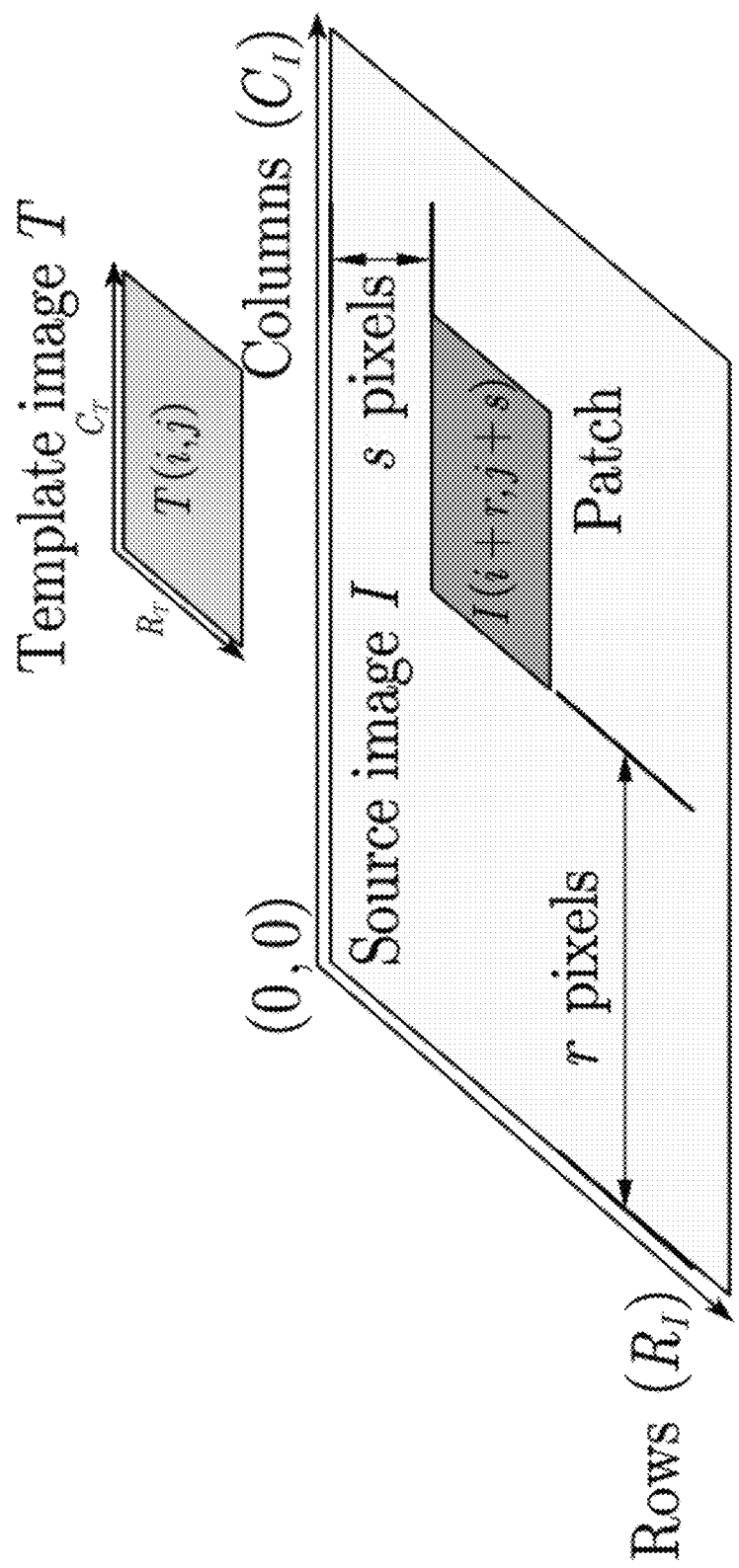
FIG. 9 shows the geometric model for illustrating template matching.

FIG. 9 shows the geometry and illustration of template matching. The patch I(i+r, j+s) is moved across the source image I by an offset (r, s) and used to calculate the similarity to the template image T(i, j).

Figure 10:
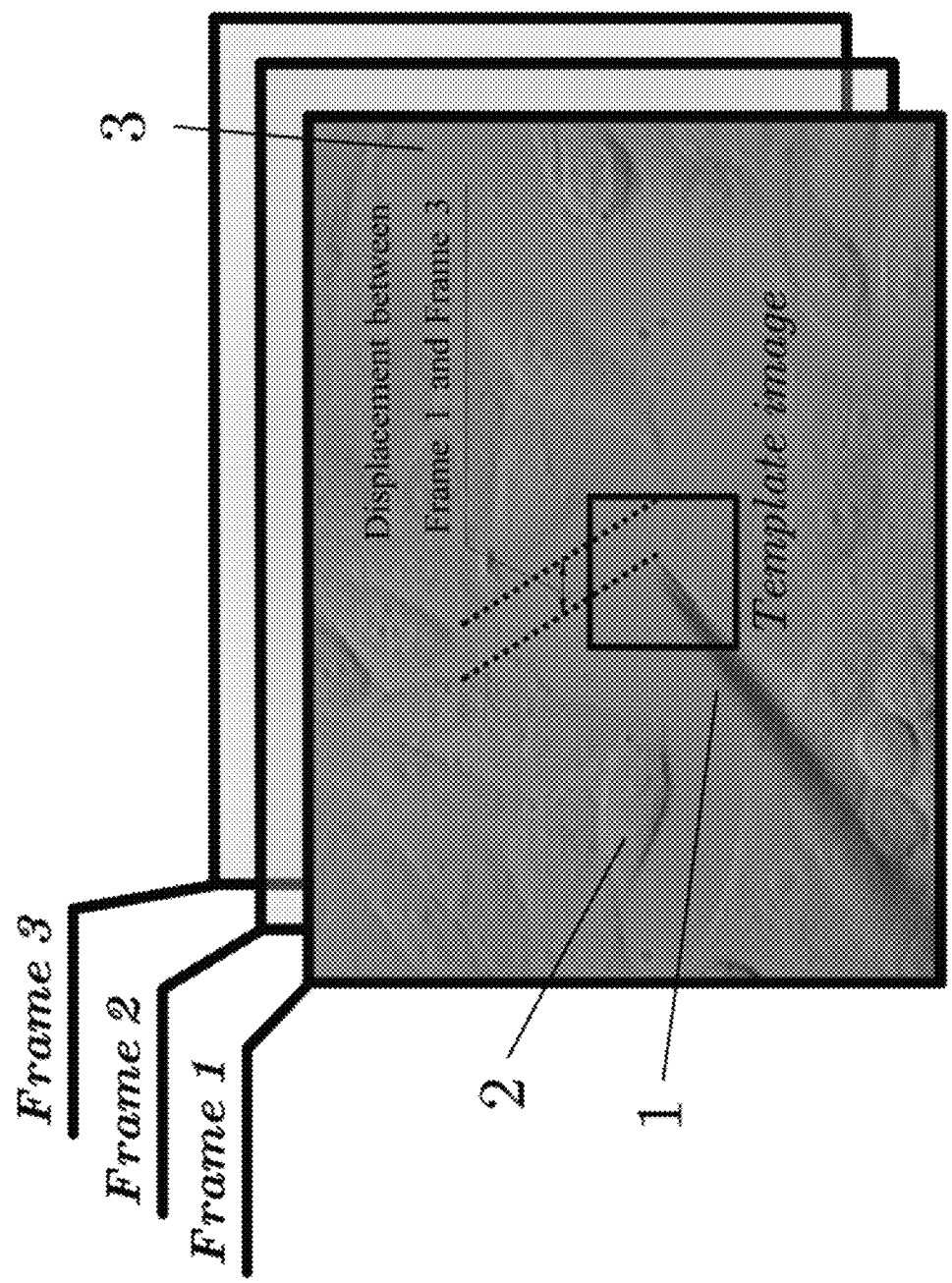
FIG. 10 shows how a home-made program matches the template image of the micropipette tip to every source image.

FIG. 10 shows how the home-made program matches the template image of the micropipette tip to every source image. First, the operator collects a template image T of the tip in focus. Second, a source image I is compared against the template image T to find a match. We use the OpenCV function matchTemplate to identify the matching area. The function matchTemplate selects a patch at every location in a source image and calculates the similarity between that patch and the template image, and then stores the similarity in the result matrix $d_E(r, s)$. The similarity is calculated by adding up squared differences in the pixel intensities of the template image T(i, j) and those of a patch in the source image I(i+r, j+s) at every location (r, s), as expressed in (11):

$$d_E(r, s) = \sum_{i=0}^{C_I} \sum_{j=0}^{R_I} [I(i+r, j+s) - T(i, j)]^2, \quad (11)$$

where (r, s) is in the range $[0, C_I] \times [0, R_I]$. After obtaining the result matrix $d_E$(r, s), the function minAlaxLoc searches the best similarity and finds its position as the location of the tip in the pixel coordinate frame. These matching locations are recorded temporarily, and every other location of the matching results (every frame 1 and frame 3) are compared to determine if the tip touches the bottom. Third, the micropipette is lowered down at a constant speed of 1 μm/s. Finally, the micropipette is retracted immediately as soon as the position difference from the second step exceeded a threshold; at the same time, positions of the tip and the stage were both determined.

One advantageous feature of the system 19 is that insertion depths of the micropipettes 1, 3 are adaptively adjustable according to a moving plane of the dish holder plate 82 of the motorized stage 8. The moving plane is used for characterizing unevenness between a focus plane of the optical microscope 12 and a moving trajectory of the motorized stage 8. Ideally, the moving plane is a horizontal plane (with respect to the reference vertical direction 900) such that no adjustment to the insertion depths of the micropipettes 1, 3 is required. Practically, however, the moving plane is not perfectly horizontal so that adaptive adjustment of the insertion depths of the micropipettes 1, 3 is advantageous. Such adaptive adjustment is realizable by automatically making contact between the individual micropipette and the dish bottom of the Petri dish 6 and by fitting the data into a virtual plane. Preferably, the one or more computers 40 are further configured to control the motorized stage 8 and the plurality of motorized micromanipulators 5, 7 in a coordinated way that the individual micromanipulator goes down or up during movement of the motorized stage 8 to compensate for the unevenness between the focus plane of the optical microscope 12 and the moving trajectory of the motorized stage 8. To achieve this purpose, it is required to determine the moving plane for characterizing the aforesaid unevenness.

Figure 11:
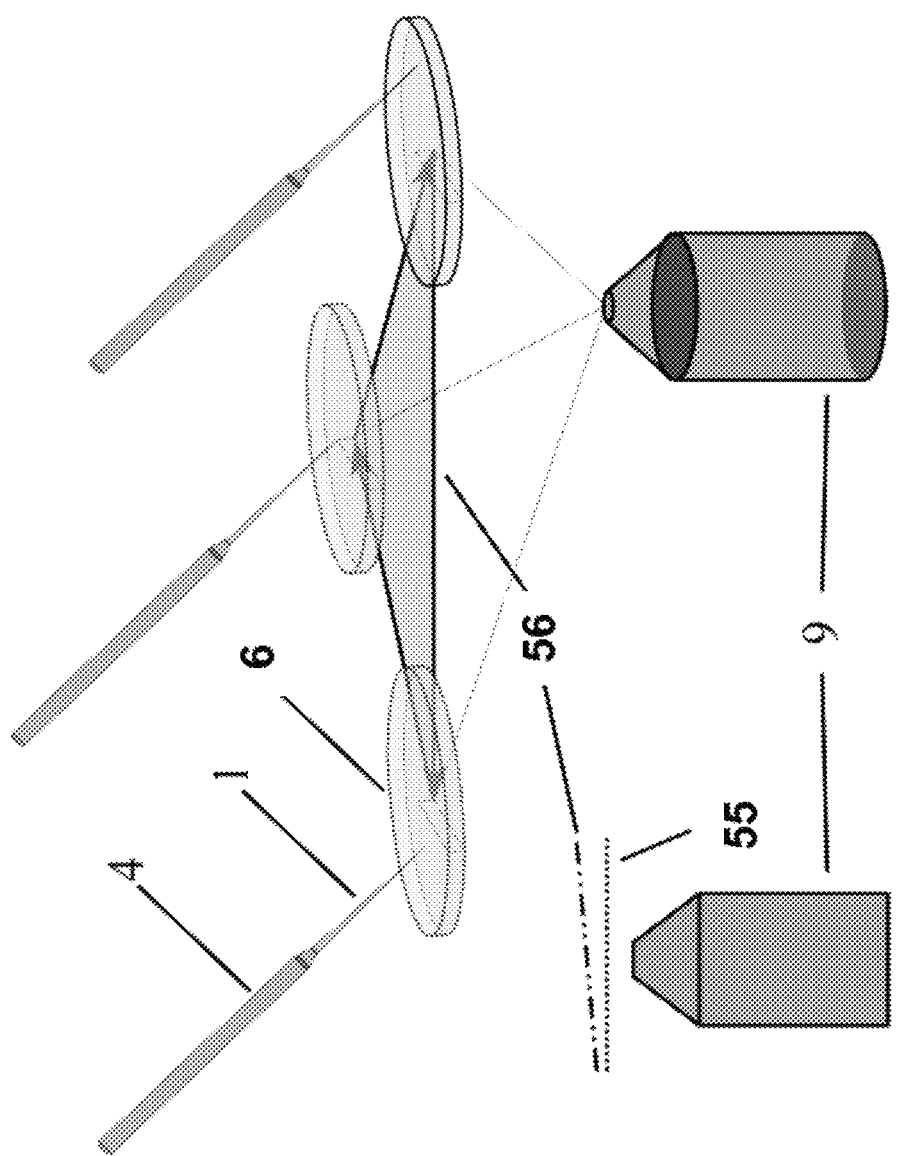
FIG. 11 shows the identification of a moving plane of a dish holder plate for adaptively adjusting a penetration depth of micropipette.

FIG. 11 shows the determination of the moving plane of the dish holder plate 82 for adaptively adjusting the penetration depth of the micropipette. The moving plane has a reference numeral of 56 while the focus plane of the optical microscope 12 is referenced as 55. We use the least-square method to identify the moving plane 56 based on stage positions $(X_i, Y_i)_{i=i, \ldots, m}$ and tip depths $(z_i)_{i=1, \ldots, m}$. The formula of the moving plane 56 is $z = PX + QY + R$, where P, Q and R are unknown scalars to be determined. To avoid ill-conditioned numerical calculations, we calculated the averages $\overline{X} = m^{-1}\sum_{i=1}^{m} X_i$, $\overline{Y} = m^{-1}\sum_{i=1}^{m} Y_i$ and $\overline{z} = m^{-1}\sum_{i=1}^{m} z_i$ first and substituted the calculated averages into the original plane formula to form a new plane formula $\hat{z} = P\hat{X} + Q\hat{Y} + \hat{R}$, where $\hat{z} = z - \overline{z}$, $\hat{X} = X - \overline{X}$, $\hat{Y} = Y - \overline{Y}$ and $\hat{R} = R + P\overline{X} + Q\overline{Y} - \overline{z}$. The best fit occurs only when the sum of the squared errors between the depths $\hat{z}_i$ and the plane values $P\hat{X}_i + Q\hat{Y}_i + \hat{R}$ is minimized. The sum (the error function) is written as $$e(P, Q, \hat{R}) = \sum_{i=1}^{m} \left[(P\hat{X}_i + Q\hat{Y}_i + \hat{R}) - \hat{z}_i\right]^2. \quad (12)$$

Equation (12) is non-negative and reaches the minimum only when every partial derivative evaluated at $P_{best}$, $Q_{best}$ and $\hat{R}_{best}$ equals zero, i.e. $\partial e/\partial P|_{P=P_{best}} = 0$, $\partial e/\partial Q|_{Q=Q_{best}} = 0$ and $\partial e/\partial \hat{R}|_{\hat{R}=\hat{R}_{best}} = 0$. These partial derivatives can be written as $$0 = \sum_{i=1}^{m} [(P_{best}\hat{X}_i + Q_{best}\hat{Y}_i + \hat{R}_{best}) - \hat{z}_i]\hat{X}_i, \quad (13)$$

$$0 = \sum_{i=1}^{m} [(P_{best}\hat{X}_i + Q_{best}\hat{Y}_i + \hat{R}_{best}) - \hat{z}_i]\hat{Y}_i \quad (14)$$

and $$0 = \sum_{i=1}^{m} [(P_{best}\hat{X}_i + Q_{best}\hat{Y}_i + \hat{R}_{best}) - \hat{z}_i]. \quad (15)$$

Rearrangement of (13) to (15) leads to the following equation:

$$\begin{bmatrix} \sum \hat{X}_i^2 & \sum \hat{X}_i\hat{Y}_i & \sum \hat{X}_i \\ \sum \hat{X}_i\hat{Y}_i & \sum \hat{Y}_i^2 & \sum \hat{Y}_i \\ \sum \hat{X}_i & \sum \hat{Y}_i & m \end{bmatrix} \begin{bmatrix} P_{best} \\ Q_{best} \\ \hat{R}_{best} \end{bmatrix} = \begin{bmatrix} \sum \hat{z}_i\hat{X}_i \\ \sum \hat{z}_i\hat{Y}_i \\ \sum \hat{z}_i \end{bmatrix}. \quad (16)$$

The matrix at the left-hand side of (16) is $$\begin{bmatrix} \sum (X_i - \bar{X})^2 & \sum (X_i - \bar{X})(Y_i - \bar{Y}) & 0 \\ \sum (X_i - \bar{X})(Y_i - \bar{Y}) & \sum (Y_i - \bar{Y})^2 & 0 \\ 0 & 0 & m \end{bmatrix} \quad (17)$$

and the right-hand side of (16) is $$\begin{bmatrix} \sum (z_i - \bar{z})(X_i - \bar{X}) \\ \sum (z_i - \bar{z})(Y_i - \bar{Y}) \\ 0 \end{bmatrix}. \quad (18)$$

Here we define $\alpha = \Sigma(X_i-\bar{X})^2$, $\gamma = \Sigma(Y_i-\bar{Y})^2$, $\beta = \Sigma(X_i-\bar{X})(Y_i-\bar{Y})$, $\psi = \Sigma(z_i-\bar{z})(X_i-\bar{X})$ and $\zeta = \Sigma(z_i-\bar{z})(Y_i-\bar{Y})$. Then (16) becomes $$\begin{bmatrix} \alpha & \beta & 0 \\ \beta & \gamma & 0 \\ 0 & 0 & m \end{bmatrix} \begin{bmatrix} P_{best} \\ Q_{best} \\ \hat{R}_{best} \end{bmatrix} = \begin{bmatrix} \psi \\ \zeta \\ 0 \end{bmatrix}. \quad (19)$$

Finally, we have $$P_{best} = (\gamma\psi - \beta\zeta)/(\alpha\gamma - \beta^2), \quad (20)$$

$$Q_{best} = (\alpha\zeta - \beta\psi)/(\alpha\gamma - \beta^2) \quad (21)$$

and $$\hat{R}_{best} = \bar{z} - P_{best}\bar{X} - Q_{best}\bar{Y}. \quad (22)$$

The formula for the moving plane 56 is then given by $$z = P_{best}(X - \bar{X}) + Q_{best}(Y - \bar{Y}) + \bar{z}. \quad (23)$$

Some experimental results, which were obtained by using the system 19 for microinjection, are listed as follows for demonstrating the effectiveness of the present invention.

Figure 12:
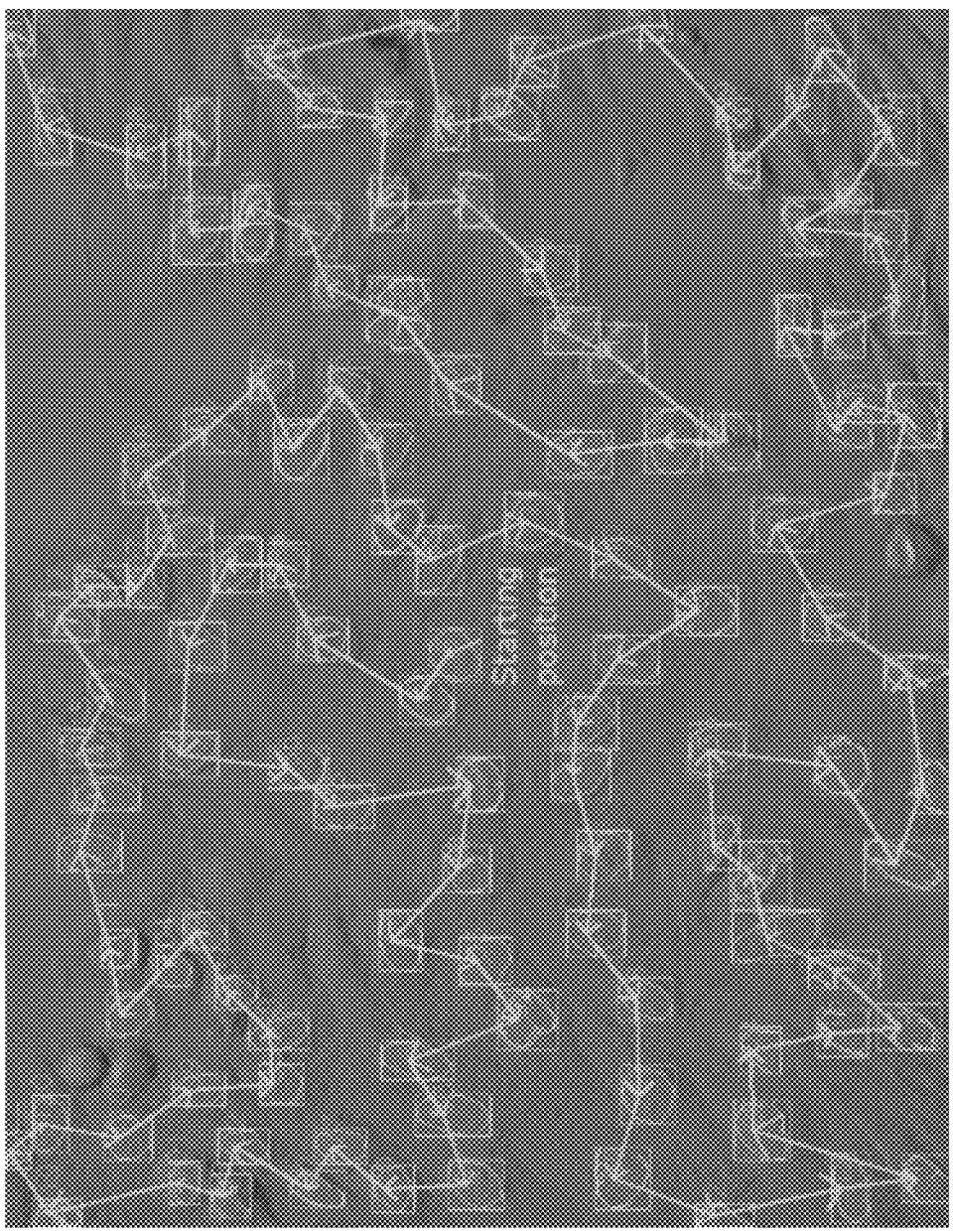
FIG. 12 shows an example of an optimized injection path of one micropipette injecting over one hundred cells under 20× magnification.

FIG. 12 shows an example of an optimized injection path of one micropipette injecting over one hundred cells under 20× magnification.

Figure 13:
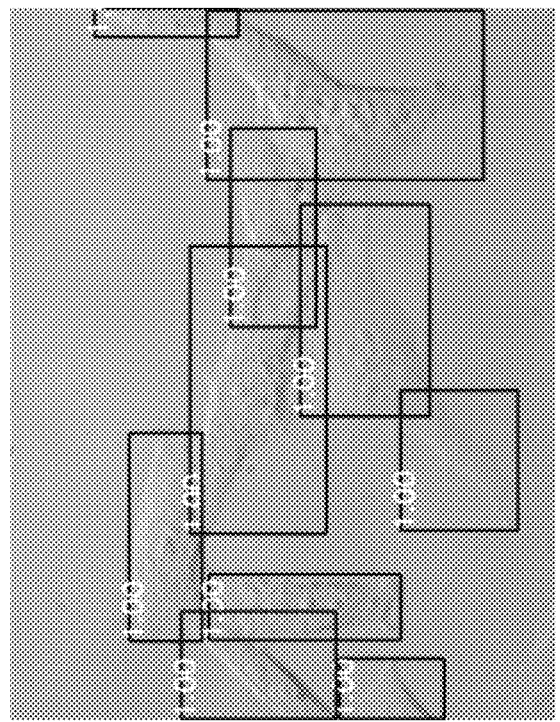
FIG. 13 shows an example of cell detection results as obtained by a cell detection algorithm, where detected cells are delineated by rectangles and marked with a confidence score.

FIG. 13 shows the cell detection results, in which detected cells are delineated by rectangles and marked with a confidence score. A deep learning algorithm is used to detect cells automatically. A total of 771 DIC images of Hep G2 cells from the microscope under 40× magnification is sampled. All images were resized to 1152×864 pixels and then annotated manually by experts. Conventionally, these data should be divided into three subsets: the training set to train different algorithms (models) to check the convergence; the validation set to evaluate the trained algorithms and tune the algorithms' hyperparameters (e.g., layers of an algorithm); and the test set to evaluate the generalization ability of a trained algorithm. We chose two algorithms in advance and split the overall image set into two subsets: the training set containing 617 randomly selected images; and the test set containing all the rest images. Data augmentation, such as flipping, random contrast distortion, and brightness distortion, was used to teach the algorithm the desired invariance and robustness properties when only 617 training samples were available.

For cell detection, the algorithm output predictions consist of bounding boxes (positions) of cells and confidence scores of the bounding boxes. For every valid prediction, the maximum IoU of the bounding box b and all ground-truth bounding boxes $b_i^g$, were calculated to determine the correspondence of a predicated bounding box b and a ground-truth bounding box $b^g$:

$$IoU(b, b^g) = \max_i \frac{\text{area}(b \cap b_i^g)}{\text{area}(b \cup b_i^g)}, \sim i = 1, 2, \ldots, m. \quad (24)$$

A prediction is considered a true positive only when its IoU is larger than a threshold $\alpha$; otherwise, it is considered a false positive. The precision-recall curve was drawn by varying the threshold $\alpha$. We calculated the AP at different IoU threshold $\alpha$ as the mean precision p at 11 recall (r) levels (0, 0.1, . . . , 1) by using the 11-point interpolation metric in:

$$AP = \frac{1}{11} \sum_{i \in \{0, 0.1, \ldots, 1\}} \max(p(r \geq l)). \quad (25)$$

Figure 15:
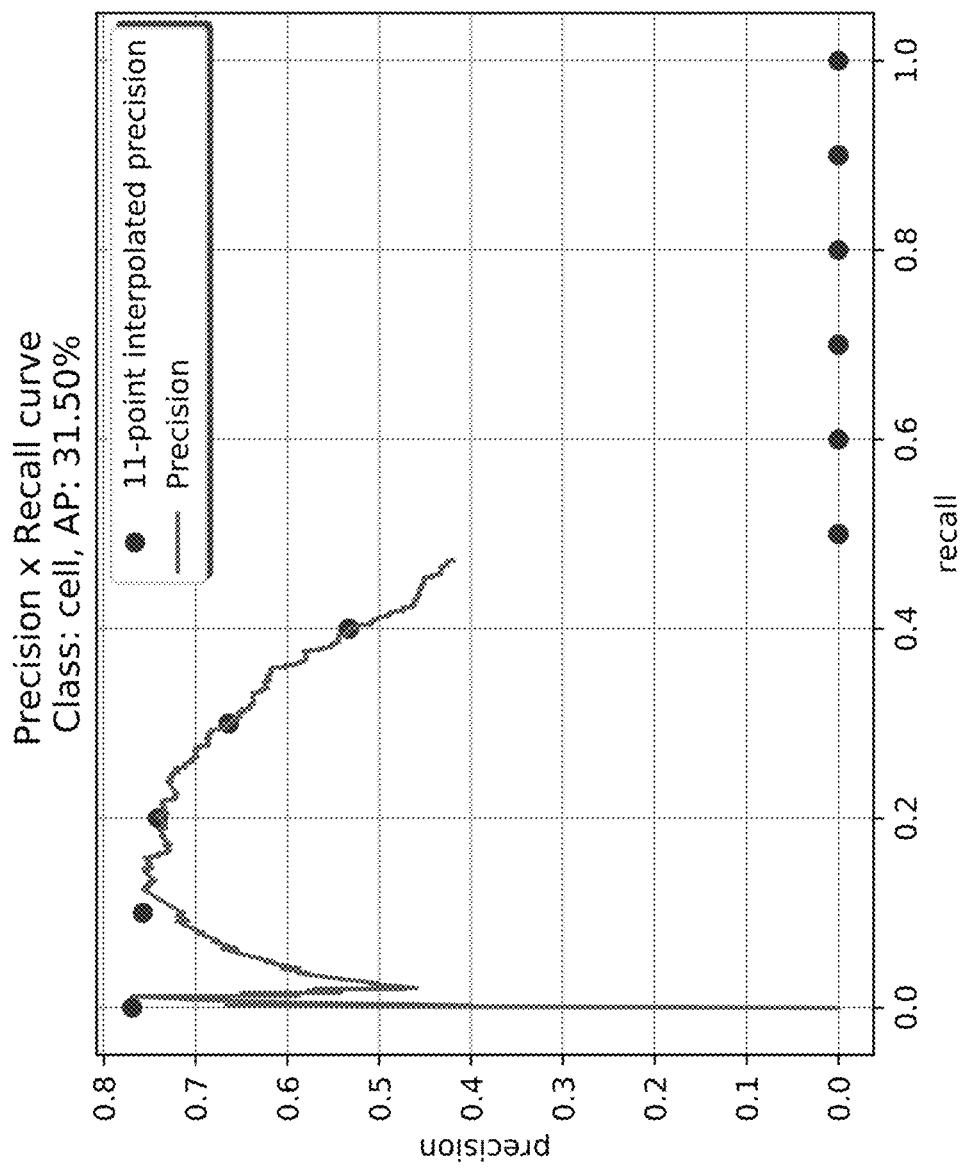
FIG. 15 shows a precision-recall curve generated at IoU threshold $\alpha=0.5$ of the cell detection algorithm.
Figure 16:
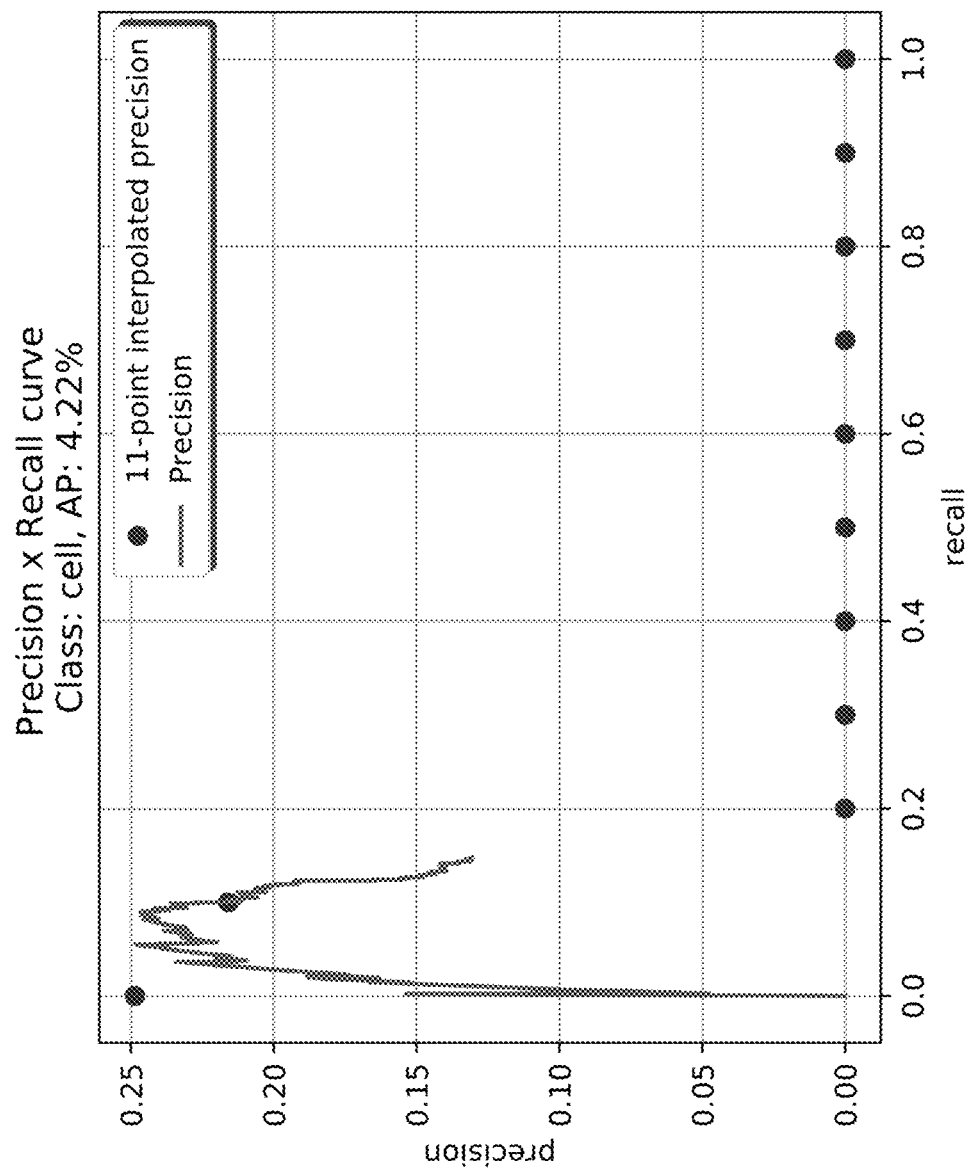
FIG. 16 shows a precision-recall curve generated at IoU threshold α=0.7 of the cell detection algorithm.

The precision-recall curves of the cell detection algorithm are provided in FIG. 15 and FIG. 16.

Figure 14:
FIG. 14 shows an example of cell semantic segmentation results by an image segmentation algorithm, where segmented cells are marked in white.

FIG. 14 shows the cell semantic segmentation results, in which segmented cells are marked white. For cell semantic segmentation, five MATLAB metrics were used to evaluate the results: global accuracy, mean accuracy, mean IoU, weighted IoU, and mean BF score. The global pixel accuracy is the ratio of correctly categorized pixels to the total number of pixels in all test images. The accuracy refers to the percentage of correctly labeled pixels for each category, that is, the cell or background in an image, while the mean accuracy is the average accuracy of all categories in all images. The IoU is the ratio of correctly labeled pixels to the total number of ground truth and predicted pixels in that category, while the mean IoU is the average IoU of all categories in all images. The weighted IoU is the average IoU of each category weighted by the number of pixels in that category. The BF score measures the alignment of the predicted boundary for each category with the ground truth, while the mean BF score is the average BF score of all categories in all images. Detailed evaluations of the cell segmentation algorithm are summarized in Table 1.

TABLE 1

| Evaluation of Cell Semantic Segmentation. | | | | |
|---|---|---|---|---|
| Global Accuracy | Mean Accuracy | Mean IoU | Weighted IoU | Mean BF Score |
| 95.331% | 83.338% | 72.455% | 88.219% | 68.438% |

FIG. 15 shows the precision-recall curve generated at IoU threshold α=0.5 of the cell detection algorithm.

FIG. 16 shows the precision-recall curve generated at IoU threshold α=0.7 of the cell detection algorithm.

Figure 17:
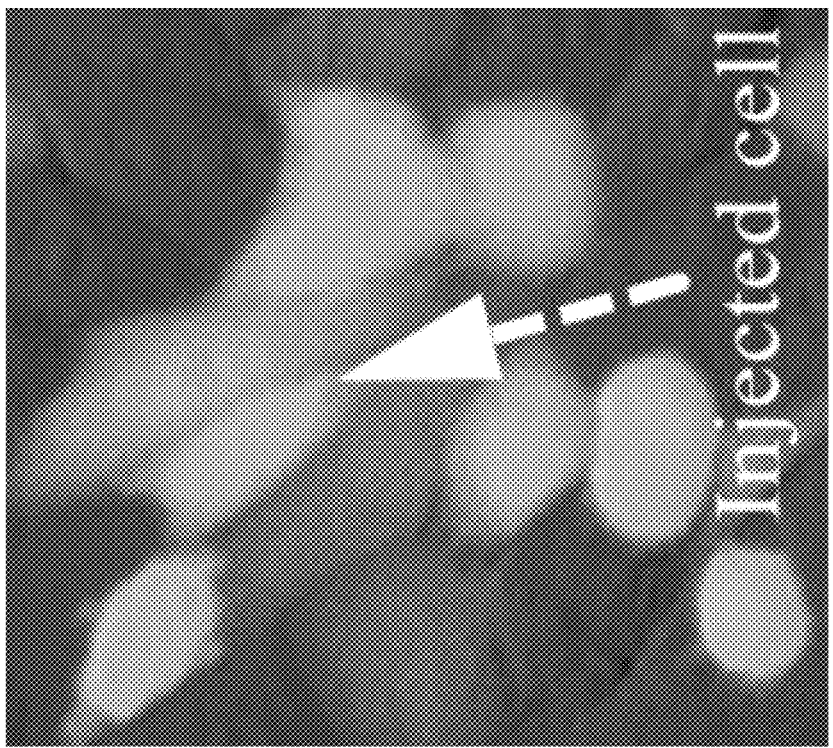
FIG. 17 shows a result of cells successfully injected with FITC.

FIG. 17 shows the result of cells successfully injected with FITC. FITC, a typical fluorescent dye, was injected into MC3T3 fibroblast cells to evaluate the success and survival rates. FITC is impermeable to cell membranes and dissolves quickly in the medium, so only successfully injected cells were counted for evaluation purposes. The concentration of FITC was 0.5 mg/mL, the output pressure for injection was 1.0 psi, the insertion duration was 100 ms, and the cell density was retained at approximately 30 to 40 cells per FOV under 40× magnification. The time interval between the two injections was set to 0.8 s, and the interval between two segments (FOV) was set to 2 s. Under such circumstances, a one-hour experiment can usually contain about 110 segments and around 4,000 cells, i.e. (3, 600−2×100)/0.8=4225≈4000.

Figure 18:
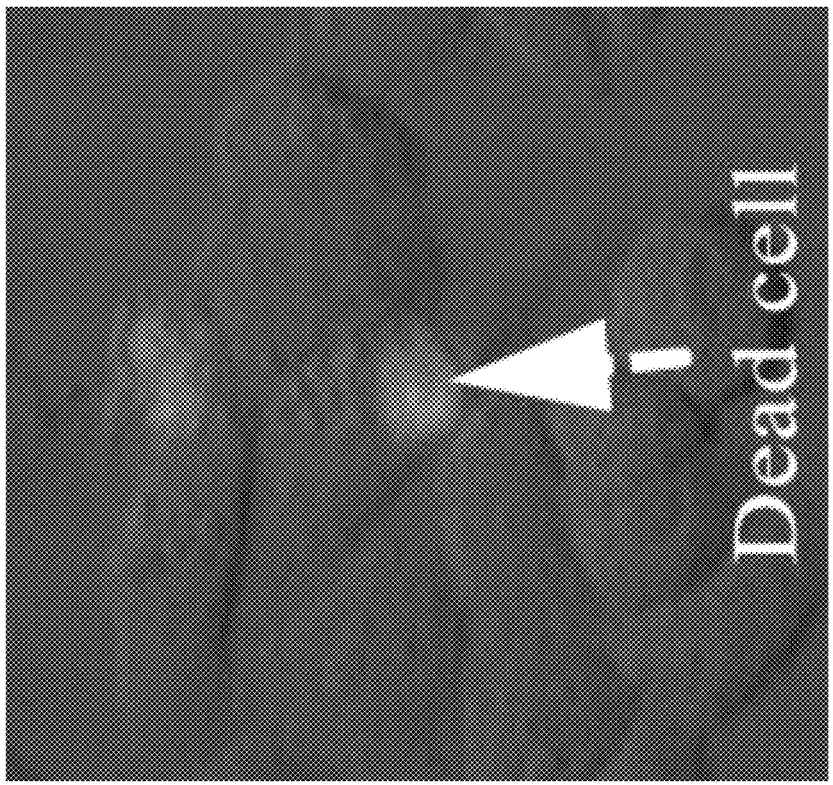
FIG. 18 shows a result of dead cells stained by PI.

FIG. 18 shows the result of dead cells stained by PI. Cells were washed with fresh medium and returned to the incubator as soon as experiments were completed. The cells were stained with PI, a fluorescent cell viability indication dye, to examine the survival rate after 30 minutes. FITC emits green fluorescent light (525 nm) under the excitation of cyan laser (488 nm) while PI emits red fluorescent light (617 nm) under the excitation of green laser (535 nm) and only binds to the DNA of the dead cells. Viable and dead cells were counted by moving the dish one segment at a time and stitching captured images together. The success and survival rates are counted according to (26) and (27), respectively:

$$\text{Success rate} = \frac{\text{Number of green fluorescent cells}}{\text{Number of injections}} \quad (26)$$

and $$\text{Survival rate} = \frac{\text{Number of red fluorescent cells}}{\text{Number of injections}}. \quad (27)$$

Table 2 summarizes the experimental results. A total of 11,857 injections were made, among which 7,147 were successfully injected, and 5,861 cells were still alive after 30-minute re-incubation. The success rate and the survival rate were 60.3% and 82.0%, respectively.

TABLE 2

| Cell Microinjection Results. | | | | | | |
|---|---|---|---|---|---|---|
| Trial number | Time | Injection number | Injected cells | Survived Cells | Success rate | Survival rate |
| 1 | 60 min | 3,748 | 2,187 | 1,596 | 58.4% | 73.0% |
| 2 | 60 min | 4,085 | 2,445 | 2,315 | 59.9% | 94.6% |
| 3 | 60 min | 4,024 | 2,515 | 1,950 | 62.5% | 77.5% |
| Total | 180 min | 11,857 | 7,147 | 5,861 | 60.3% | 82.0% |

Lastly, a summary of non-limiting advantages offered by the system 19 is provided as follows. First, the system 19 can automatically detect unstained cells by using the deep learning technology. Second, the system 19 can optimize the injection path of tens to hundreds of cell positions in a short time. Third, the system 19 can inject cells continuously for a long time (currently about an hour) with two micropipettes by using constant outflow-based injection and adjusting the penetration depth adaptively according to the moving plane 56, whereas many existing microinjection systems cannot ensure long time working without changing micropipettes. Fourth, the system 19 can achieve automated high-throughput microinjection of adherent cells based on the first three advantages.

The present invention may be embodied in other specific forms without departing from the spirit or essential characteristics thereof. The present embodiment is therefore to be considered in all respects as illustrative and not restrictive. The scope of the invention is indicated by the appended claims rather than by the foregoing description, and all changes that come within the meaning and range of equivalency of the claims are therefore intended to be embraced therein.

What is claimed is:

1. A system for automatically providing microinjection of a sample to a plurality of adherent cells, the plurality of adherent cells being disposed on a Petri dish, the system comprising:

a motorized stage for two-dimensionally moving the Petri dish;

a plurality of motorized micromanipulators for manipulating a plurality of micropipettes used for injecting the sample to the plurality of adherent cells, an individual micromanipulator being configured to hold and manipulate a respective micropipette in the plurality of micropipettes;

a gas pressure provider connectable to an individual micropipette for controllably forcing out the sample present in the individual micropipette;

an optical microscope for viewing the Petri dish disposed on the motorized stage;

a camera for capturing a cell image containing the plurality of adherent cells as viewed through the optical microscope; and one or more computers for controlling the system, the one or more computers being configured to:

control the motorized stage to sequentially visit respective cells in the plurality of adherent cells according to an injection sequence, wherein the injection sequence is an optimized one selected by minimizing a total distance traveled by the motorized stage to sequentially visit the respective cells such that each of the respective cells is visited once by one micropipette selected from the plurality of micropipettes, whereby when the respective cells are randomly distributed on the Petri dish, using the plurality of micropipettes reduces the minimized total distance over using a single micropipette to thereby increase a throughput of microinjection;

when a certain cell in the plurality of adherent cells is visited by a certain micropipette manipulated by a corresponding micromanipulator, control the corresponding micromanipulator to cause said certain micropipette to pierce into said certain cell, and control the gas pressure provider to cause said certain micropipette to inject a predetermined amount of the sample into said certain cell;

obtain XY locations of micropipette tips of the plurality of micropipettes;

control the camera to capture the cell image;

determine, from the cell image, XY locations of the respective cells; and determine the injection sequence according to the XY locations of micropipette tips of the plurality of micropipettes and the XY locations of the respective cells;

wherein the injection sequence is determined by a process comprising:

constructing an undirected graph G=(V, E) wherein:

$V=\{node(l)|l=0, 1, \ldots, nq\}$ is a set of nq+1 nodes, n being a number of cells in the plurality of adherent cells, q being a number of micropipettes in the plurality of micropipettes, V being partitioned into n clusters of nodes, the n clusters of nodes being denoted as $V_0, V_1, \ldots, V_n$, the q micropipettes being denoted as $P_1, P_2, \ldots, P_q$;

$E=\{e_{ij}|i, j=0, 1, \ldots, nq\}$ is an edge set representing edges joining node(i) and node(j) with a cost $c_{ij}$ in the graph G;

$V_0$ is given by $V_0=\{node(0)\}$ where node(0) represents $P_1$;

$V_m$, $m\in\{1, 2, \ldots, n\}$, is given by $V_m=\{node((m-1)q+k)|k=1, 2, \ldots, q\}$, where node((m−1)q+1), node((m−1)q+2), . . . , node(mq) respectively represent $C_m, C'_m(2), C'_m(3), \ldots, C'_m(q)$ in which $C_m$ is an mth real cell in the plurality of adherent cells, and $C'_m(k)$, $k\in\{2, \ldots, q\}$, is a kth virtual cell of the mth real cell;

$P_k$, $k\in\{1, 2, \ldots, q\}$, has a coordinate $(u_{P_k}, v_{P_k})$ determined from the XY locations of the micropipette tips;

$C_m$, $m\in\{1, 2, \ldots, m\}$, has a coordinate $(u_m, v_m)$ determined from the XY locations of the respective cells;

$C'_m(k)$, $k\in\{2, \ldots, q\}$, has a coordinate $(u'_m(k), v'_m(k))$ given by $(u'_m(k), v'_m(k))=(u_m+u_{P_1}-u_{P_k}, v_m+v_{P_1}-v_{P_k})$; and $c_{ij}$, $i, j\in\{1, 2, \ldots, nq\}$, is given by a Euclidean distance between node(i) and node(j);

numerically solving an equality-generalized traveling salesman problem (E-GTSP) defined by G to identify an ordered sequence of nodes containing one node from each of $V_0, V_1, \ldots, V_n$ such that the ordered sequence of nodes forms a minimum cost cycle; and obtaining the injection sequence from the ordered sequence of nodes.

2. The system of claim 1, wherein the optical microscope is a fluorescence microscope.

3. The system of claim 1, wherein the optical microscope is an inverted microscope.

4. The system of claim 1 further comprising a plurality of manually rotatable stages for mounting the plurality of motorized micromanipulators.

5. The system of claim 1, wherein the individual micromanipulator comprises a stainless-steel micropipette holder for holding the respective micropipette.

6. The system of claim 1, wherein the one or more computers are further configured to, in determining the XY locations of the respective cells, use a deep learning-based algorithm to perform image segmentation on the respective cells.

7. The system of claim 1, wherein the plurality of motorized micromanipulators consists of two micromanipulators such that q=2.

8. The system of claim 1, wherein the solving of the E-GTSP comprises:

transforming the E-GTSP to an asymmetric traveling salesman problem (TSP);

transforming the asymmetric TSP into a symmetric TSP; and solving the symmetric TSP to yield the ordered sequence of nodes.

9. The system of claim 1, wherein the one or more computers are further configured to, after microinjection of the plurality of adherent cells is completed, control the motorized stage to move such that the optical microscope originally viewing a first segment of the Petri dish switches to viewing a second segment thereof, the first segment containing the plurality of adherent cells, the second segment containing a next plurality of adherent cells for microinjection after completion of microinjection of the plurality of adherent cells.

* * * * *